(12) United States Patent
El Saadawi et al.

(10) Patent No.: US 12,278,015 B2
(45) Date of Patent: Apr. 15, 2025

(54) APPLICATION-SPECIFIC PROCESSING OF A DISEASE-SPECIFIC SEMANTIC MODEL INSTANCE

(71) Applicant: Realyze Intelligence, Inc., Pittsburgh, PA (US)

(72) Inventors: Gilan El Saadawi, Pittsburgh, PA (US); Aaron Brauser, Gibsonia, PA (US); Gary Wallace, Harrisville, PA (US)

(73) Assignee: Realyze Intelligence, Inc., Pittsburgh, PA (US)

( * ) Notice: Subject to any disclaimer, the term of this patent is extended or adjusted under 35 U.S.C. 154(b) by 0 days.

(21) Appl. No.: 18/633,994

(22) Filed: Apr. 12, 2024

(65) Prior Publication Data
US 2024/0266070 A1    Aug. 8, 2024

Related U.S. Application Data

(63) Continuation of application No. 18/489,437, filed on Oct. 18, 2023, now Pat. No. 11,961,622.
(Continued)

(51) Int. Cl.
*G06F 40/30* (2020.01)
*G06F 7/00* (2006.01)
(Continued)

(52) U.S. Cl.
CPC ............ *G16H 50/50* (2018.01); *G06F 16/28* (2019.01); *G06F 16/90335* (2019.01);
(Continued)

(58) Field of Classification Search
CPC ........ G16H 50/50; G16H 50/20; G16H 50/70; G16H 10/60; G16H 10/40; G16H 15/00;
(Continued)

(56) References Cited

U.S. PATENT DOCUMENTS

| 8,612,261 B1 * | 12/2013 | Swanson | G16H 40/67 |
| | | | 705/3 |
| 11,621,081 B1 * | 4/2023 | O'Keefe | G16H 50/30 |
| | | | 705/3 |

(Continued)

FOREIGN PATENT DOCUMENTS

| CN | 116844686 A | * | 10/2023 | |
| EP | 4233851 A1 | * | 8/2023 | ............. A61K 31/00 |

OTHER PUBLICATIONS

Office Action (Final Rejection) dated May 1, 2024 for U.S. Appl. No. 18/489,412 (pp. 1-9).
(Continued)

*Primary Examiner* — Jeffrey P Aiello
(74) *Attorney, Agent, or Firm* — Blueshift IP; Robert Plotkin

(57) ABSTRACT

A computer-implemented method and system are applied to a first instance of a first disease-specific semantic model. The method and system: receive a first request; process the first instance of the first disease-specific semantic model based on the first request to generate a first processed instance of the first disease-specific semantic model; and provide the first processed instance of the first disease-specific semantic model as output.

16 Claims, 14 Drawing Sheets

Related U.S. Application Data

(60) Provisional application No. 63/418,099, filed on Oct. 21, 2022.

(51) Int. Cl.

| | | |
|---|---|---|
| *G06F 16/28* | (2019.01) | |
| *G06F 16/903* | (2019.01) | |
| *G06F 17/00* | (2019.01) | |
| *G06F 18/10* | (2023.01) | |
| *G06F 18/22* | (2023.01) | |
| *G06F 40/20* | (2020.01) | |
| *G06F 40/40* | (2020.01) | |
| *G16H 10/20* | (2018.01) | |
| *G16H 10/60* | (2018.01) | |
| *G16H 15/00* | (2018.01) | |
| *G16H 50/20* | (2018.01) | |
| *G16H 50/50* | (2018.01) | |
| *G16H 50/70* | (2018.01) | |

(52) U.S. Cl.
CPC .............. *G06F 17/00* (2013.01); *G06F 18/10* (2023.01); *G06F 18/22* (2023.01); *G06F 40/20* (2020.01); *G06F 40/30* (2020.01); *G06F 40/40* (2020.01); *G16H 10/20* (2018.01); *G16H 10/60* (2018.01); *G16H 15/00* (2018.01); *G16H 50/20* (2018.01); *G16H 50/70* (2018.01)

(58) Field of Classification Search
CPC .... G06F 16/28; G06F 16/903; G06F 16/9032; G06F 16/90335; G06F 17/00; G06F 40/20; G06F 40/30; G06F 40/40; G16B 40/20; G16B 5/20; G01N 2800/52
USPC ................. 700/1, 90; 702/19, 181, 1; 703/2; 705/2, 3; 707/999.003, 999.1, 708
See application file for complete search history.

(56) References Cited

U.S. PATENT DOCUMENTS

| | | | |
|---|---|---|---|
| 11,759,358 | B2* | 9/2023 | Dorin .................... A61F 9/008 606/6 |
| 2013/0332191 | A1* | 12/2013 | Hoffman ................ G06Q 30/02 705/3 |
| 2018/0046780 | A1* | 2/2018 | Graiver .................. G06F 40/44 |
| 2018/0157800 | A1* | 6/2018 | Ravishankar .......... G16H 50/50 |
| 2018/0285743 | A1* | 10/2018 | Bringsjord ......... G06Q 30/0185 |
| 2021/0050075 | A1* | 2/2021 | Hao ....................... G16H 50/20 |
| 2021/0357769 | A1* | 11/2021 | Vrouwenvelder ..... G16H 40/67 |
| 2022/0171946 | A1* | 6/2022 | Xu ............................ G06N 3/08 |
| 2022/0261668 | A1* | 8/2022 | Stumpe ................. G06F 16/284 |
| 2022/0374605 | A1* | 11/2022 | Sethi ..................... G06T 19/006 |
| 2024/0006073 | A1* | 1/2024 | Holdmann ............. G16H 20/40 |
| 2024/0112765 | A1* | 4/2024 | Tse ........................ G16H 10/20 |
| 2024/0135108 | A1 | 4/2024 | El Saadawi |
| 2024/0136065 | A1* | 4/2024 | El Saadawi ........... G16H 50/70 |
| 2024/0233958 | A9 | 7/2024 | El Saadawi |
| 2024/0233960 | A9 | 7/2024 | El Saadawi |

OTHER PUBLICATIONS

Office Action (Final Rejection) dated Jun. 13, 2024 for U.S. Appl. No. 18/489,577 (pp. 1-37).

Office Action dated Dec. 29, 2023 for U.S. Appl. No. 18/489,412 (pp. 1-16).

Office Action dated Feb. 15, 2024 for U.S. Appl. No. 18/489,577 (pp. 1-31).

Office Action (Non-Final Rejection) dated Sep. 5, 2024 for U.S. Appl. No. 18/489,577 (pp. 1-48).

* cited by examiner

FROM

Condition Valueset — 922

| Code System | Code | Display |
|---|---|---|
| SNOMEDCT_US | 417509001 | Visceral dysfunction (finding) |
| SNOMEDCT_US | 24526004 | Inflammatory bowel disease |
| SNOMEDCT_US | 737195007 | Crohn disease of upper gastrointestinal tract (disorder) |
| SNOMEDCT_US | 34000006 | Crohn's disease (disorder) |
| SNOMEDCT_US | 426549001 | Crohn's disease in remission (disorder) |
| SNOMEDCT_US | 265607002 | Crohn's disease of esophagus (disorder) |
| SNOMEDCT_US | 722850002 | Crohn's disease of gastrointestinal anastomosis (disorder) |
| SNOMEDCT_US | 234999001 | Crohn's disease of gingivae (disorder) |
| SNOMEDCT_US | 196578009 | Crohn's disease of oral soft tissues (disorder) |
| SNOMEDCT_US | 402376005 | Crohn's disease of penis (disorder) |
| SNOMEDCT_US | 70622003 | Crohn's disease of pyloric antrum (disorder) |
| SNOMEDCT_US | 61424003 | Crohn's disease of pylorus (disorder) |
| SNOMEDCT_US | 402377001 | Crohn's disease of scrotum (disorder) |
| SNOMEDCT_US | 427910000 | Diverticulitis of sigmoid colon (disorder) |
| SNOMEDCT_US | 56165008 | Diverticulitis of small intestine (disorder) |
| SNOMEDCT_US | 722845008 | Diverticulitis of small intestine with complication (disorder) |
| SNOMEDCT_US | 722846009 | Diverticulitis of small intestine without complication (disorder) |
| ICD10CM | K50 | Crohn disease |
| ICD10CM | K52 | Other and unspecified noninfectious gastroenteritis and colitis |
| ICD10CM | K51 | Ulcerative Colitis |

Co-morbidities Valueset — 924

| Code System | Code | Display |
|---|---|---|
| SNOMEDCT_US | 2492009 | Nutritional disorder |
| SNOMEDCT_US | 414916001 | Obesity(disorder) |
| SNOMEDCT_US | 404684003 | Severe obesity |
| SNOMEDCT_US | 238136002 | Morbid obesity (disorder) |
| SNOMEDCT_US | 271737000 | Anemia |
| SNOMEDCT_US | 74732009 | Mental disorder (disorder) |
| SNOMEDCT_US | 66214007 | Substance abuse (disorder) |
| LOINC | 718-7 | Hb lab value |
| LOINC | 39156-5 | BMI range |

Example Valuesets of IBD (Module 120)

FROM FIG. 9C

FIG. 9D

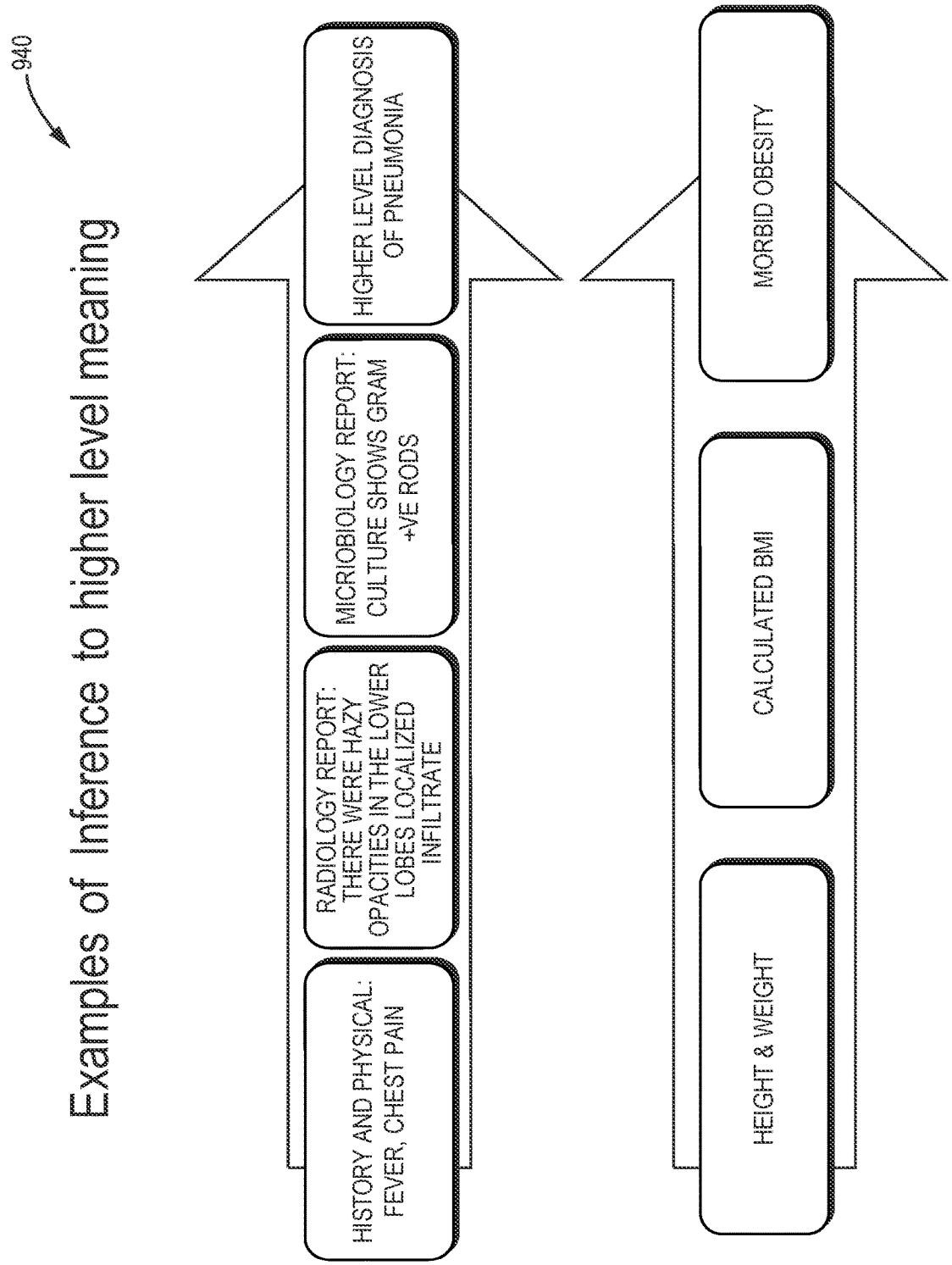

APPLICATION-SPECIFIC PROCESSING OF A DISEASE-SPECIFIC SEMANTIC MODEL INSTANCE

CROSS-REFERENCE TO RELATED APPLICATIONS

This application is a continuation of U.S. patent application Ser. No. 18/489,437, filed on Oct. 18, 2023, entitled, "Application-Specific Processing of a Disease-Specific Semantic Model Instance," which claims priority to U.S. Prov. Pat. App. No. 63/418,099, filed on Oct. 21, 2022, entitled, "Patient Disease Model Generation and Maintenance Method and System," all of which are hereby incorporated by reference herein.

BACKGROUND

When a healthcare provider provides healthcare services to a patient in a patient encounter, the provider must create accurate, precise, and complete clinical documentation in order to provide the patient with high quality care, and in order for the provider to receive proper and timely payment for services rendered. Yet creating clinical documentation in a form that is clear, comprehensive, and relevant to the people and systems that consume such documentation is challenging, especially as new information becomes available over time. For example, one problem with existing systems is that they tend to log isolated, individual data points related to a single episode of care for the patient. Such a narrow focus obscures the broader health conditions of the patient. As a result, both human healthcare providers and automated healthcare systems find themselves confronted with a dense forest of data and struggle to discern the patient's overall health status, and past and current conditions, as well as their progression.

For example, when creating clinical documentation, a variety of information typically is recorded, such as acts, findings, and observations about the patient's history, current physiological state, treatment options, and the need for medical follow-up. Physicians and other healthcare providers typically document a patient encounter in a clinical note, which may be stored in any of a variety of formats. For example, the clinical note may be stored in plain (unstructured) text, a structured document, or a combination thereof. Furthermore, information may be extracted from the clinical note, manually and/or automatically, and stored in discrete data fields, such as in an Electronic Health Record (EHR) associated with the patient. As the patient participates in multiple healthcare encounters over time, the number and variety of records of the patient's encounters accumulate. Such records may be in disparate formats, such as unstructured text, structured text, and database (e.g., EHR) records. Such records may be stored in multiple systems, which may or may not communicate with each other. The volume, variety, and dispersion of such records makes it difficult for the patient and the patient's healthcare providers to obtain an understanding of the patient's health, such as the progression of specific diseases with which the patient has been diagnosed, over time. Furthermore, the patient's healthcare records may contain evidence of health conditions that remain undiagnosed due to the difficulty of integrating and analyzing the contents of those records over time.

What is needed, therefore, are systems and methods that address these limitations of the existing state of the art.

SUMMARY

A computer-implemented method and system are applied to a first instance of a first disease-specific semantic model. The method and system: receive a first request; process the first instance of the first disease-specific semantic model based on the first request to generate a first processed instance of the first disease-specific semantic model; and provide the first processed instance of the first disease-specific semantic model as output.

Other features and advantages of various aspects and embodiments of the present invention will become apparent from the following description and from the claims.

BRIEF DESCRIPTION OF THE DRAWINGS

FIGS. 9C-9D are diagrams illustrating the use of value sets to generate a patient-specific instance of a disease-specific semantic disease model, and a summary of that patient-specific instance, according to one embodiment of the present invention.

FIG. 9E is a diagram illustrating examples of making interferences to a higher level meaning according to one embodiment of the present invention.

DETAILED DESCRIPTION

Figure 1:
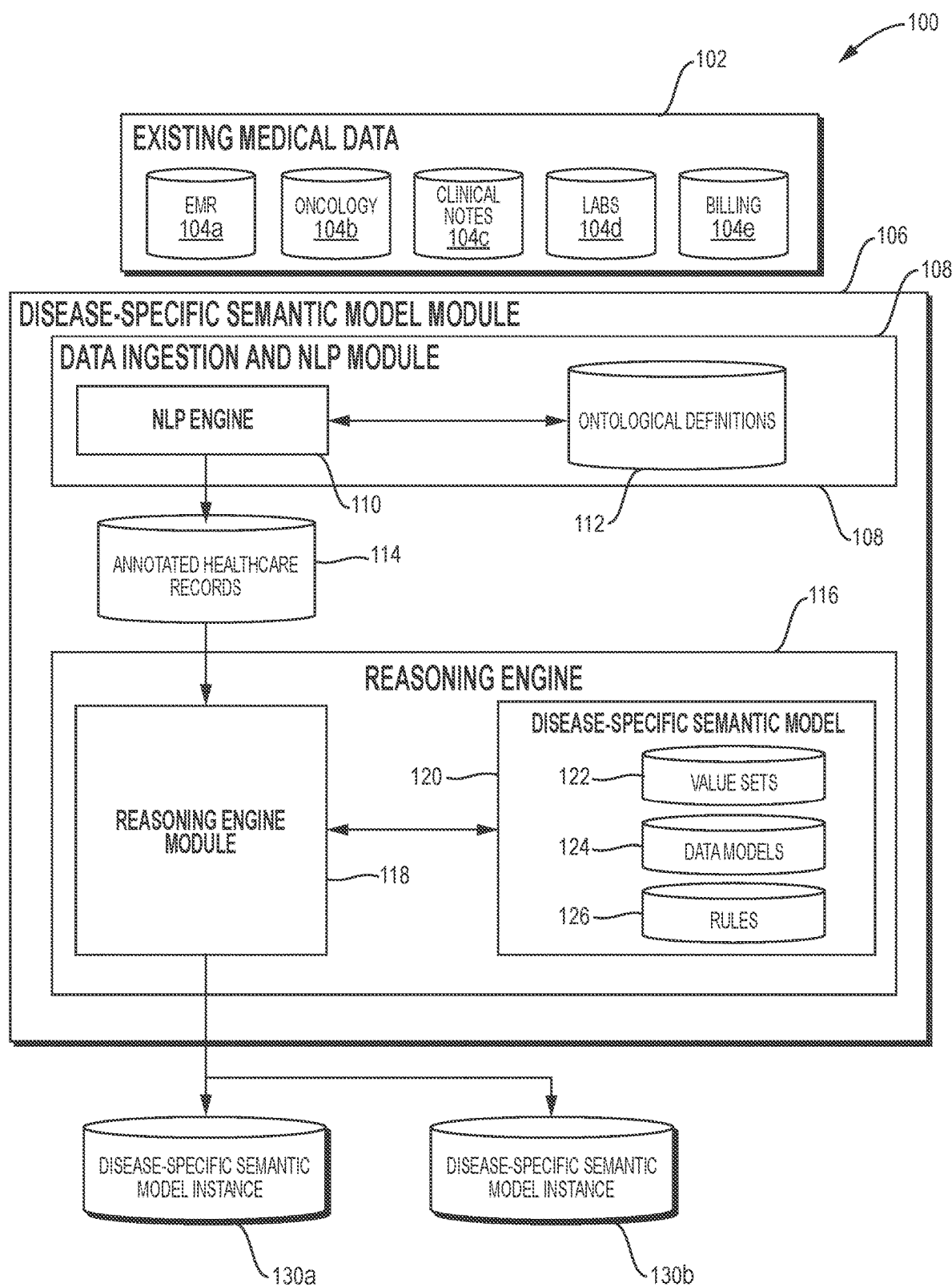
FIG. 1 is a dataflow diagram of a system for generating an instance of a disease-specific semantic model according to one embodiment of the present invention.
Figure 2:
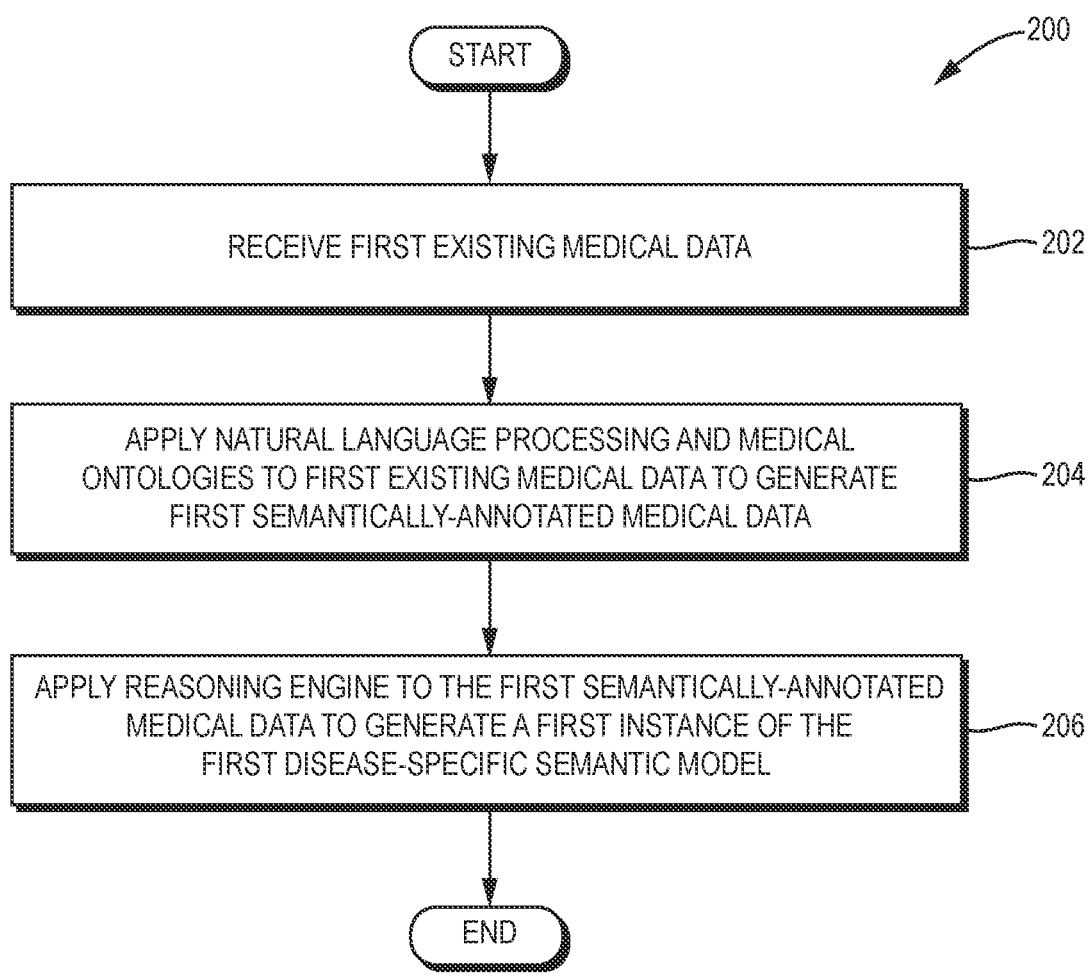
FIG. 2 is a flowchart of a method performed by the system of FIG. 1 according to one embodiment of the present invention.

Referring to FIG. 1, a dataflow diagram is shown of a system 100 for performing various operations on a disease-specific semantic model according to one embodiment of the present invention. Referring to FIG. 2, a flowchart is shown of a method 200 performed by the system 100 of FIG. 1 according to one embodiment of the present invention.

The system 100 includes existing medical data 102, which may include any of a variety of medical data relating to a plurality of patients, including a patient referred to herein as a first patient. For example, the existing medical data 102 may include electronic medical record (EMR) data 104a containing one or more EMRs associated with the first patient, oncology data 104b associated with the first patient, one or more clinical notes 104c describing one or more encounters with the first patient, lab reports 104d representing results of one or more laboratory tests performed on the first patient, and one or more billing records 104e associated with the first patient. These are merely examples of kinds of the existing medical data 102 that the system 100 may include. More generally, the existing medical data 102 may include any kind of medical data, in any form, that contains information about and/or relating to the first patient. The existing medical data 102 may for example, include unstructured data (e.g., freeform text) and/or structured data (e.g., XML data and/or database records) in any combination. Furthermore, the system 100 may include similar data for any number of additional patients. Therefore, any reference herein to the existing medical data 102 in relation to the first patient should be understood to be equally applicable to the same or similar medical data in relation to any number of patients, either individually or in aggregate.

The system 100 may include a disease-specific semantic model module 106, which may perform a variety of functions disclosed herein. For example, the disease-specific semantic model module 106 may receive some or all of the existing medical data 102 (FIG. 2, operation 202). Although FIG. 2 shows such receipt of the existing medical data 102 as a single operation, more generally the disease-specific semantic model module 106 may receive any portion(s) of the existing medical data 102 over time. For example, as will be described in more detail below, any portion of the existing medical data 102 may change over time, and the disease-specific semantic model module 106 may receive as input some or all of the resulting changed existing medical data 102 and perform any of the functions disclosed herein on such changed existing medical data 102.

The disease-specific semantic model module 106 may include a data ingestion and natural language processing (NLP) module 108, which may include an NLP engine 110 and medical ontologies 112. The data ingestion and NLP module 108 may receive some or all of the existing medical data 102, and the NLP engine 110 may apply natural language processing and the medical ontologies 112 to the existing medical data 102 to generate first semantically-annotated medical data 114 associated with the first patient (FIG. 2, operation 204). Because of the NLP engine 110's use of the medical ontologies 112, the first semantically-annotated medical data 114 contains semantic annotations that are medicine-specific. As a result, the first semantically-annotated medical data 114 includes not only the kind of structured data (e.g., tags) that would be produced by a generic NLP engine, but also semantic annotations that are based on the medical ontologies 112, and which imbue the first semantically-annotated medical data 114 with medical meanings. The NLP engine 110 may use any of a variety of known NLP techniques to perform the functions disclosed herein, including using one or more language models (e.g., one or more Large Language Models (LLMs)) to perform at least some of operation 204.

Although some or all of the structured data in the first semantically-annotated medical data 114 may be generated by the NLP engine 110, some of the structured data in the first semantically-annotated medical data 114 may be obtained from other sources. For example, data in the existing medical data 102 may be structured data, and may be included in the first semantically-annotated medical data 114. As this illustrates, the first semantically-annotated medical data 114 may include some structured data that was generated by the NLP engine 110 and some structured data that was not generated by the NLP engine 110 (e.g., that was received from another source, such as the existing medical data 102). Similarly, although some or all of the semantically-annotated data in the first semantically-annotated medical data 114 may be generated by the NLP engine 110 using the medical ontologies 112, some of the semantically-annotated data in the first semantically-annotated medical data 114 may be obtained from other sources, such as sources within the existing medical data 102. As this illustrates, the first semantically-annotated medical data 114 may include some semantically-annotated data that was generated by the NLP engine 110 and some semantically-annotated data that was not generated by the NLP engine 110.

The disease-specific semantic model module 106 may also include a reasoning engine 116, which may include a reasoning engine module 118 and a disease-specific semantic model 120. As will be described in more detail below, the disease-specific semantic model 120 may model a specific disease, such as breast cancer. The disease-specific semantic model 120 includes a set of data elements (attributes, each with a range of possible values) that are sufficient to accurately capture the state of a particular disease being modeled, along with any relevant co-morbidities for any patient. The disease-specific semantic model 120 may accurately represent the relevant information (and only the relevant information) associated with a particular disease (where the definition of "relevant" might be application-or user-specific). By focusing the disease-specific semantic model 120 on a narrow set of data elements that are relevant to the disease models by the disease-specific semantic model, embodiments of the present invention enable increases in the sensitivity and specificity of target applications in comparison to more generic prior art approaches.

For example, a generic medical model might try to identify any bit of medical information in narrative text, not knowing the purpose for which that piece of information is to be used. As a result, such a generic model will misidentify and overlook pieces of information, leading to false positives and/or false negatives with respect to a given target disease and target application. In contrast, the disease-specific semantic model 120 homes on only the relevant data elements, based on a particular definition of relevance specified by the disease-specific semantic model 120. As a result, the disease-specific semantic model 120 "knows" what information it needs, and where to find that information, ignoring other medical information that might be valuable in other contexts, but not for the given target disease and target application).

Although only one such disease-specific semantic model 120 is shown in FIG. 1, the system 100 may include any number of additional such disease-specific models, each of which may model a distinct disease. As a result, any description herein of the disease-specific semantic model 120 and functions that are performed in connection with the disease-specific semantic model 120 should be understood to be applicable to any number of disease-specific semantic models representing any number of distinct diseases.

The disease-specific semantic model 120 may include a plurality of value sets 122, a plurality of data models 124, and a plurality of rules 126. Although the plurality of value sets 122, the plurality of data models 124, and the plurality of rules 126 are shown as components of the disease-specific semantic model 120, any one or more of these may be implemented externally to the disease-specific semantic model 120. For example, at least some of the plurality of rules 126 may be implemented externally to the disease-specific semantic model 120 and may be shared among a plurality of disease-specific models.

The reasoning engine 116 may apply the reasoning engine module 118 to the first semantically-annotated medical data 114 to generate a first instance 130a of the first disease-specific semantic model 120 (FIG. 2, operation 206). As will be described in more detail below, this may include assigning at least one value to at least one attribute in the disease-specific semantic model 120 to generate the first instance 130a of the first disease-specific semantic model 120. The first disease-specific semantic model 120 may include a plurality of attributes, and operation 206 may include assigning a distinct value to each of those plurality of attributes to generate the first instance 130a of the first disease-specific semantic model 120.

The first instance 130a of the first disease-specific semantic model 120 is associated with, and specific to, the first patient. The first instance 130a may for example, include and/or include information that is based on information about the first patient in the existing medical data 102. Similarly, the system 100 may generate a second instance (not shown) of the first disease-specific semantic model 120, based on information (e.g., in the existing medical data 102) that is specific to a second patient, in which case the second instance of the first disease-specific semantic model 120 may be specific to the second patient. More generally, the system 100 may use the techniques disclosed herein to generate patient-specific instances of the first disease-specific semantic model 120 (and of other disease-specific semantic models) for any number of patients.

Although FIG. 1 shows only the first disease-specific semantic model 120, which is associated with a particular disease (e.g., breast cancer), the system 100 may include a plurality of disease-specific semantic models corresponding to a plurality of distinct diseases. For example, the system 100 may include a second disease-specific model (not shown), which may correspond to a second disease (e.g., diabetes). The first and second disease-specific semantic models may for example, include at least some attributes that differ from each other. Even when two disease-specific semantic models include a common attribute (e.g., disease stage), the set of permissible values of the common attribute may differ between the two disease-specific semantic models.

For example, in the case of oncology disease specific models, multiple such models (e.g., for breast cancer, lung cancer, and prostate cancer) may have certain attributes in common, such as stage, TNM, and histology, because those attributes are relevant to all types of cancer represented by those models. Each instance of such a model, corresponding to a distinct patient, will have different values for those attributes. Some oncology disease-specific models, however, may have attributes that other oncology disease-specific models do not have. For example, both breast cancer and Prostate cancer disease-specific models may have attributes related to the BRCA gene, whereas Lung cancer disease-specific models may not have such attributes.

Figure 9A:
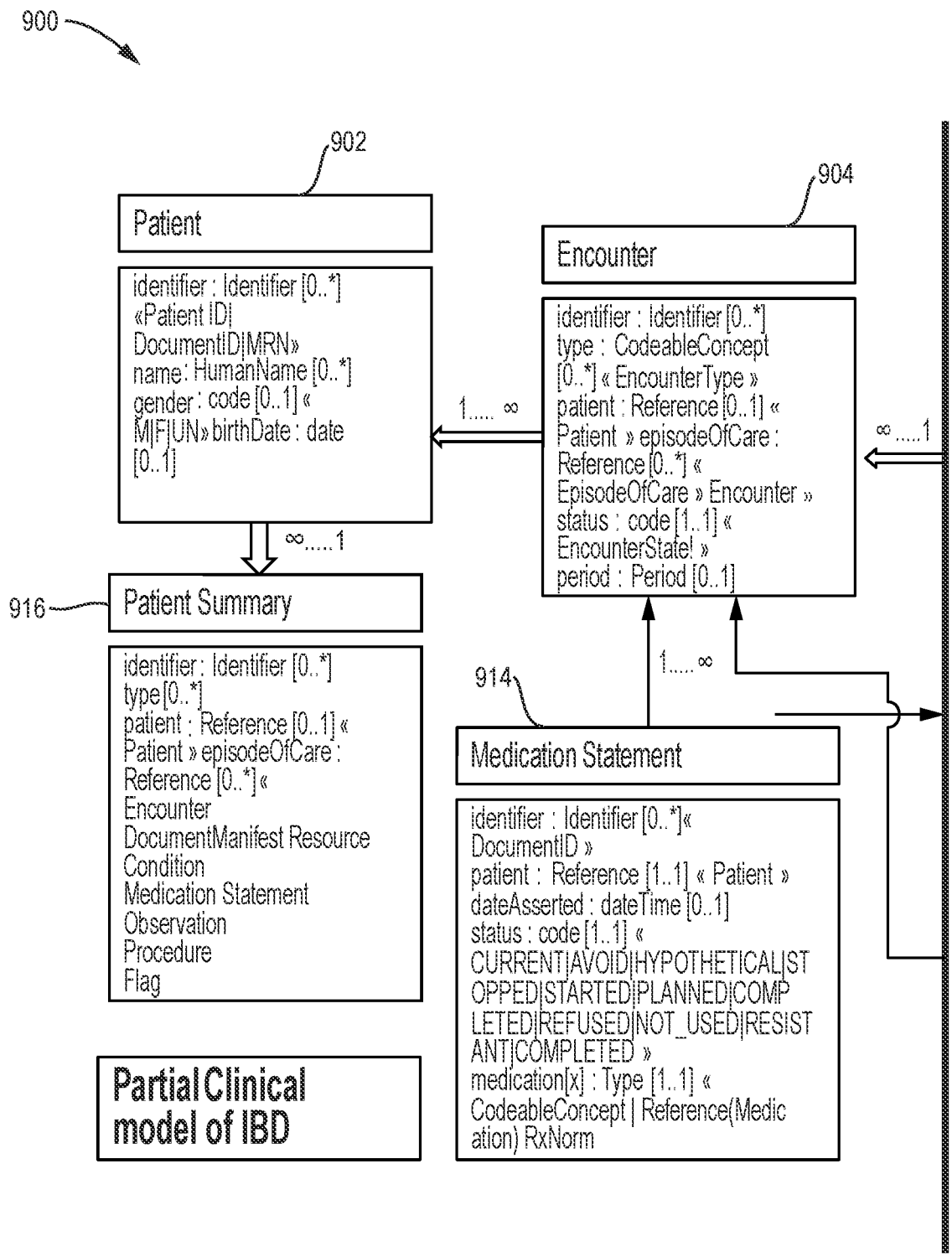
FIGS. 9A-9B are diagrams illustrating data structures that are used to create a patient-specific instance of a disease-specific semantic disease model according to one embodiment of the present invention.
Figures 9A, 9B:
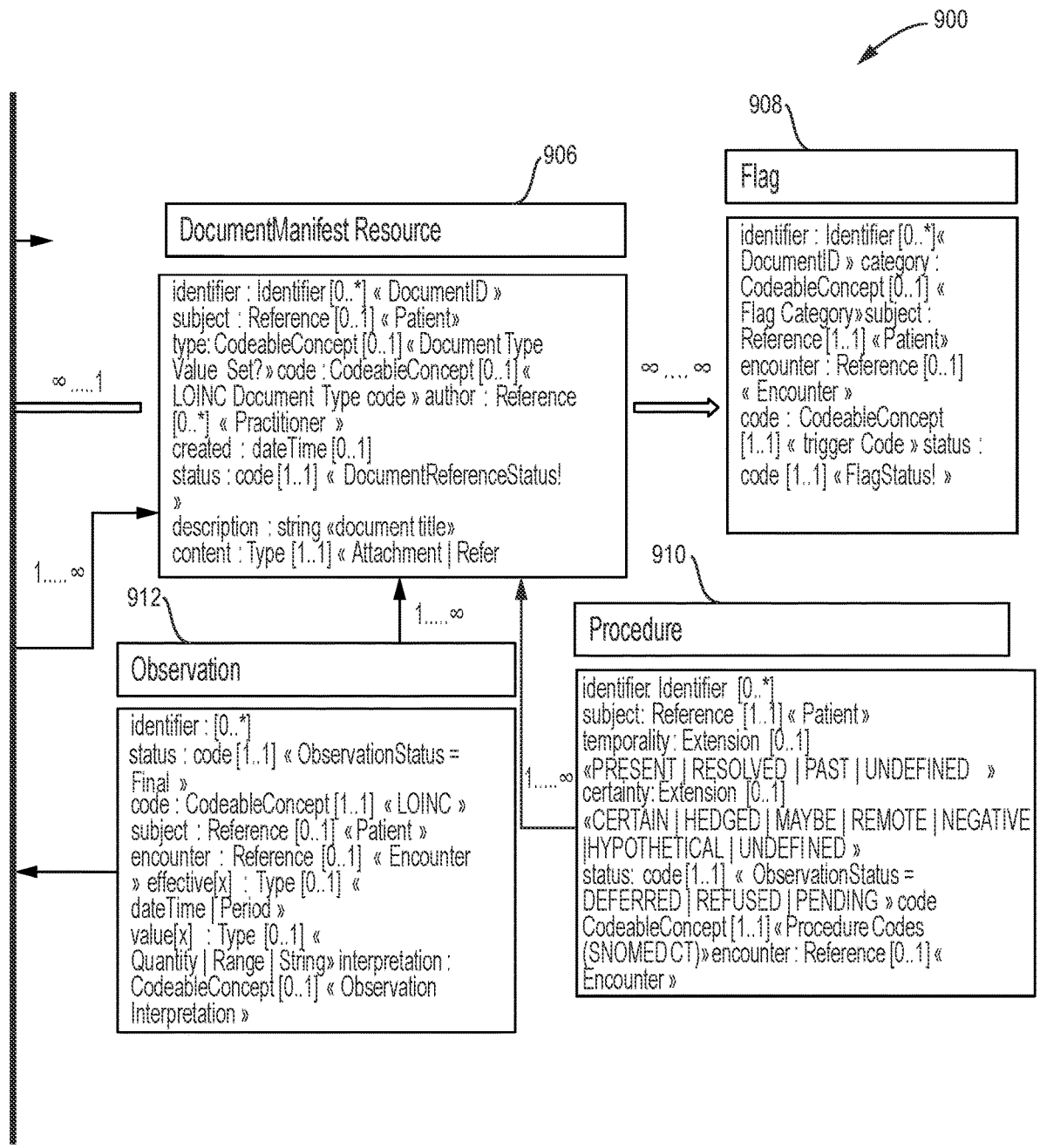

To illustrate how the system 100 and method 200 may be applied in practice more concretely, FIGS. 9A-9B show a variety of data structures which represent specific examples of various data elements of the system 100 of FIG. 1. The particular data structures shown in FIGS. 9A-9B are illustrated in simplified form and, in practice, may be larger and/or more complex than is shown in FIGS. 9A-9B.

An encounter definition 904 defines various data elements that may be instantiated to represent a particular patient encounter, such as a unique identifier, type, patient, and status associated with the encounter. The encounter definition 904 may be instantiated in one or more instances, each having specific values for the data elements in the encounter definition 904, to represent one or more corresponding patient encounters. For example, multiple instances of the encounter definition 904 may be instantiated with specific values to represent multiple encounters of a patient.

A document manifest resource definition 906 defines various data elements that may be instantiated to represent a particular clinical note as a document manifest resource, such as a unique identifier, subject, type, creation date, status, description, and content associated with the document manifest resource. The document manifest resource definition 906 may be instantiated in one or more instances, each having specific values for the data elements in the document manifest resource definition 906, to represent one or more corresponding clinical document. For example, multiple instances of the document manifest resource definition 906 may be instantiated with specific values to represent multiple document manifest resources associated with a patient.

A procedure definition 910 defines various data elements that may be instantiated to represent a particular procedure performed on a patient, such as a unique identifier, subject, temporality, certainty, and status associated with the procedure. The procedure definition 910 may be instantiated in one or more instances, each having specific values for the data elements in the procedure definition 910, to represent one or more corresponding procedures. For example, multiple instances of the procedure definition 910 may be instantiated with specific values to represent multiple procedures performed on the patient.

An observation definition 912 defines various data elements that may be instantiated to represent a particular observation of a patient, such as a unique identifier, status, code, subject, and value associated with the observation. The observation definition 912 may be instantiated in one or more instances, each having specific values for the data elements in the observation definition 912, to represent one or more corresponding observations including lab results and vital data. For example, multiple instances of the observation definition 912 may be instantiated with specific values to represent multiple observations of the first patient.

A medication statement definition 914 defines various data elements that may be instantiated to represent a particular medication statement associated with a patient, such as a unique identifier, status, and medication associated with the medication statement. The medication statement definition 914 may be instantiated in one or more instances, each having specific values for the data elements in the medication statement definition 914, to represent one or more corresponding medication statements. For example, multiple instances of the medication statement definition 914 may be instantiated with specific values to represent multiple medications associated with the first patient.

The system 100 and method 200 may perform the functions disclosed herein to generate, based on the existing medical data 102 for one or more patients, one or more instances of the encounter definition 904, the document manifest resource definition 906, the procedure definition 910, the observation definition 912, and the medication statement definition 914.

The system 900 also includes a flag definition 908, which defines various data elements that may be instantiated to represent one or more flags associated with a patient, such as a unique identifier and a code. For any particular patient, the system 100 and method 200 may for example, generate and populate the data elements in one or a plurality of such instances of the flag definition 908 based on that patient's instance(s) of the encounter definition 904, document manifest resource definition 906, procedure definition 910, observation definition 912, and medication statement definition 914.

The system 900 also includes a patient definition 902, which defines various data elements that may be instantiated to represent a particular patient, such as a unique identifier, name, gender, and birth date of the patient. The patient definition 902 may be instantiated in one or more instances, each having specific values for the data elements in the patient definition 902, to represent one or more corresponding patients. For example, a first instance of the patient definition 902 may be instantiated with particular values for the data elements shown in FIGS. 9A-9B to represent the patient that is referred to herein as the first patient. Instances of the patient definition 902 may be part of a patient-specific disease-specific model instance, such as the first instance 130*a* and/or the second instance 130*b*.

For any particular patient, the system 100 and method 200 may based on that patient's instance(s) of the encounter definition 904, document manifest resource definition 906, flag definition 908, procedure definition 910, observation definition 912, and medication statement definition 914, generate an instance of the patient definition 902 corresponding to that patient. Such an instance is an example of a disease-specific semantic model instance (e.g., the first instance 130*a* of the first disease-specific semantic model 120 shown in FIG. 1).

The system 900 also includes a patient summary definition 916, which defines various data elements that may be instantiated to represent a summary of a particular patient, such as a unique identifier, patient, condition(s), procedure(s), medication statement(s), observation(s), and procedure(s) associated with the particular patient. Within an instance of the patient summary definition 916, the patient may point to or be based on an instance of the patient definition 902; the condition(s) may point to or be based on one or more instances of a condition definition (not shown); the procedure(s) may point to or be based on one or more instances of the procedure definition 910; the medication statement(s) may point to or be based on one or more instances of the medication statement definition 914; the observation(s) may point to or be based on one or more instances of the observation definition 912; and the flag(s) may point to or be based on one or more instances of the flag definition 908.

There may be zero-to-many relationships between instances of various definitions in the system 900. For example, there may be a zero-to-many relationship between instances of the patient definition 902 and instances of the encounter definition 904, because instances of the patient definition 902 and instances of the document manifest resource definition 906, between instances of the procedure definition 910 and instances of the document manifest resource definition 906, between instances of the observation definition 912 and instances of the document manifest resource definition 906, between instances of the medication statement definition 914 and instances of the document manifest resource definition 906, and between instances of the medication statement definition 914 and instances of the encounter definition 904.

Figure 9C:
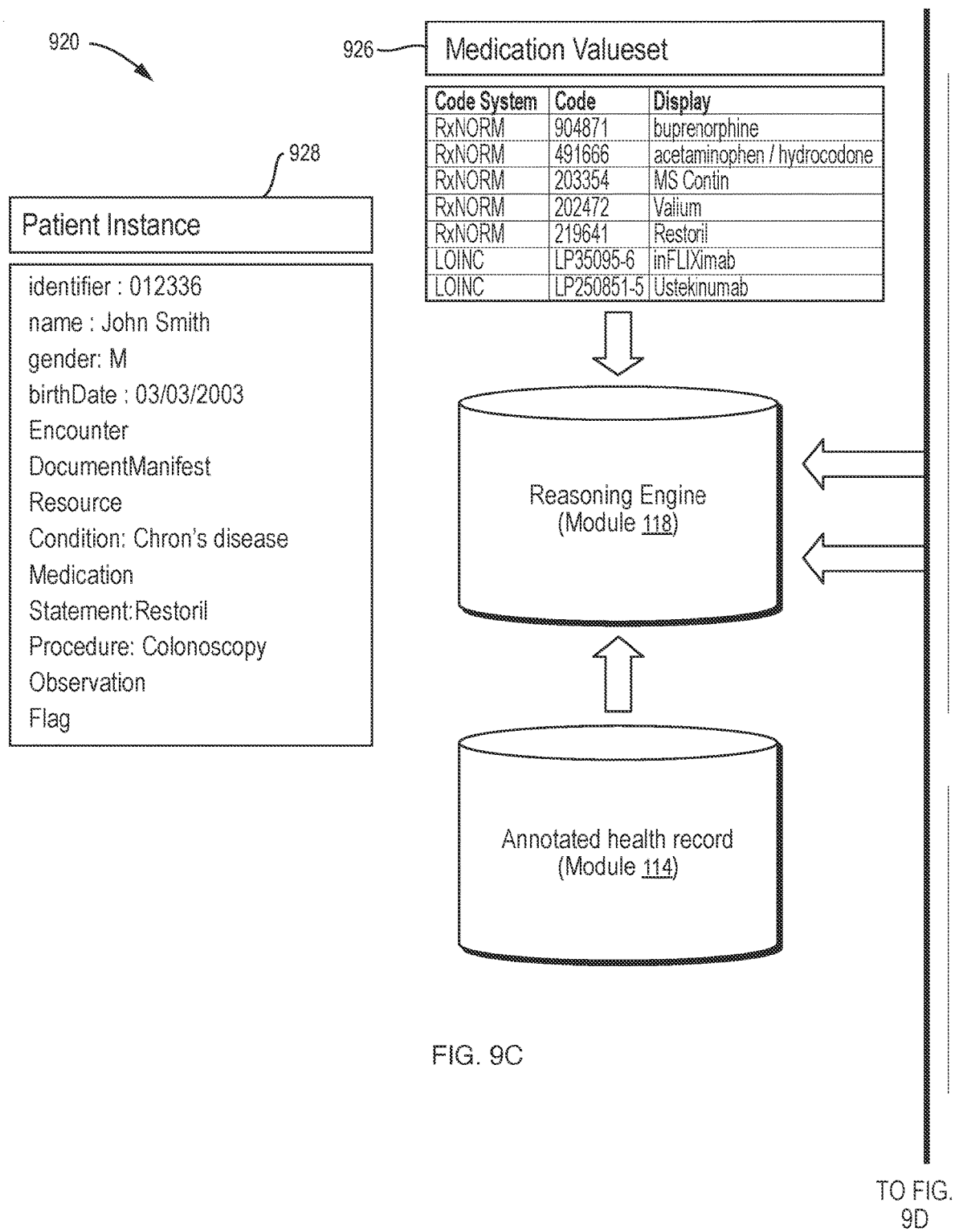

Referring to FIGS. 9C-9D, a more specific example is shown in connection with Irritable Bowel Disease (IBD). The system 920 of FIGS. 9C-9D includes three value sets: a condition value set 922 representing conditions that are examples of IBD; a co-morbidities value set 924 representing co-morbidities for IBD; and a medication value set 926 representing medications associated with IBD.

In general, each of the value sets 922, 924, and 926 contains data which enables the NLP engine 110 to map from data elements in the existing medical data to codes representing concepts in the medical ontologies 112 (e.g., SNOMED). For example, in the condition value set 922, "Inflammatory bowel disease" is mapped to the SNOMED code 24526004. As a result, if the NLP engine 110 is generating the first semantically-annotated medical data 114 for a particular patient, the NLP engine 110 may map the SNOMED code 24526004 to one or more data element(s) in the existing medical data 102 for that patient, thereby indicating that those data elements indicated that the patient has the condition "Inflammatory bowel disease." This is an example of a semantic annotation, which the NLP engine 110 may include in the first semantically-annotated medical data 114 for that patient. As described in more detail below, the reasoning engine module 118 may based on the first semantically-annotated medical data 114 (including semantic annotations generated by the NLP engine 110 in the first semantically-annotated medical data 114) and the plurality of rules 126, map codes from the medical ontologies 112 (e.g., SNOMED) representing higher-level concepts to data elements in the existing medical data 102 and/or the first semantically-annotated medical data 114.

As this example illustrates, the process of generating semantic annotations within the first semantically-annotated medical data 114 for a particular disease may make use of one or more disease-specific value sets that are associated with that particular disease. For example, the reasoning engine module 118 may use such disease-specific value sets 922, 924, and 926 to map structural annotations generated by the NLP engine 110 to semantic annotations in the first semantically-annotated medical data 114.

Furthermore, generating semantic annotations in the first semantically-annotated medical data 114 may involve more than merely mapping certain data elements (e.g., ontology codes) to other values. Generating such semantic annotations may for example, involve performing calculations and/or applying rules. In the case of obesity, for example, and as shown in FIG. 9E, the reasoning engine 116 may calculate a patient's body-mass index (BMI) based on the patient's height and weight, determine whether the patient is obese based on the patient's BMI, and store the resulting obesity determination in a structural annotation and/or semantic annotation in the first semantically-annotated medical data 114. As another example, assume that the existing medical data 102 includes a discharge note, which contains the statement: "a laparoscopic removal of a device from the abdomen was then performed." SNOMED does not contain a single concept to encode this entire statement. Instead, SNOMED only enables such a statement to be encoded into two sub-concepts, such as by encoding "laparoscope" in the code 6174004 and encoding "removal of device from abdomen" in the code 68526006. Although this might be sufficient for some applications, others might require the identification and coding of the combined statement. To do that, the system 100 may post-coordinate the two concepts as follows: 68526006 |removal of device from abdomen|:425391005| using access device|=6174004 |laparoscope|. The system 100 may also extend SNOMED by giving this new post-coordinated concept a new code.

As can be seen from the examples in FIGS. 9C-9D, a single value set may include mappings from codes in multiple ontologies (e.g., SNOMED and ICD), and both ontology codes and data in the existing medical data 102. For example, the value set 924 includes "BMI<18 or >40," which indicates that if the body mass index of obesity in the existing medical data 102 (e.g., in one of the EMRs 104a) has a value less than 18 or greater than 40, the reasoning engine module 118 will conclude that the patient has a co-morbidity for IBD. As this example also illustrates, the value sets 922, 924, and 926 may include not only specific values (e.g., ontology codes) that are mapped to specific values, but may also include ranges of values that may be mapped to other values.

The reasoning engine 116 may use the first semantically-annotated medical data 114 to generate a patient instance 928, which is an example of the first instance 130a shown in FIG. 1. The patient instance 928 in FIGS. 9C-9D has been generated, using the method 200 of FIG. 2, based on the disease-specific value sets 922, 924, and 926 to contain the specific data shown in the patient instance 928 in FIGS. 9C-9D. For example, the NLP engine identified a statement of "chronic inflammation of the GI tract" as referring to either Crohn's disease or ulcerative colitis. Both of these are contained in the model's condition value set 922 and, as a result, the reasoning engine 116 may conclude, that the first patient has IBD. As will be described in more detail below, such a conclusion that the first patient has IBD may enable embodiments of the present invention to put the first patient in a cohort with other patients having IBD.

As the above implies, the system 100 may include different value sets for different diseases. For example, a disease-specific model for breast cancer may include one or more value sets that differ from the disease-specific value sets 922, 924, and 926 shown in FIGS. 9C-9D for IBD. Each value set for a particular disease may be constructed to include only values that are relevant to that particular disease. It is in this sense that such value sets are "disease-specific."

FIG. 9E shows two examples of higher-level reasoning that the reasoning engine 116 may perform on a patient-specific instance of a disease-specific model. In the system 940 of FIG. 9E, the existing medical data 102 includes one or more documents showing that the first patient has fever and chest pain, a radiology report indicating that there are hazy opacities in the first patient's lower lobe, and a microbiology report saying the first patient has gram positive rods. The reasoning engine 116 infers, from the presence of hazy opacities in the lower lobes, that there is localized infiltrate. The reasoning engine 116 also infers, from the localized infiltrate, the chest pain, the fever, and the gram positive rods, that the first patient has pneumonia. The reasoning engine 116 may store any of these conclusions into the first instance 130a of the first disease-specific semantic model 120, for use in any of the reasoning disclosed herein.

Before describing the operation of the system 100 further, certain elements of the system 100 will be described in more detail. For example, the NLP engine 110 may be or include any kind of NLP engine, such as a general-purpose NLP engine (e.g., the Natural Language Toolkit (NLTK), spaCy, Stanford NLP, or OpenNLP), a domain-specific (e.g., medicine-specific) NLP engine (such as cTAKES, the Health Language Processing (HLP) Lab NLP, or the Linguamatics I2E), or a Large Language Model (LLM) of any kind(s).

Although only one NLP engine 110 is shown within the module 108 in FIG. 1, more generally the module 108 may include one or a plurality of NLP engines and may apply any one or more of such NLP engines to the existing medical data 102 to generate the first semantically-annotated medical data 114. As another example, the module 108 may include a plurality of NLP engines, and the module 108 may dynamically select one of the plurality of NLP engines to apply to the existing medical data 102 based on one or more of any of a variety of factors. As the module 108 applies NLP to the existing medical data 102 multiple times and/or to multiple portions of the existing medical data 102, the module 108 may select and apply different NLP engines. In this way, the module 108 may select and apply the best NLP engine at any time based on the available NLP engines and the nature of the NLP task to be performed.

The medical ontologies 112 may include, for example, structured representations of medical information which capture the entities, their attributes, and the relationships between these entities in a formalized manner. The medical ontologies 112 may include ontological definitions, which define and distinguish each concept within an ontology. Examples of medical ontologies include SNOMED CT (Systematized Nomenclature of Medicine Clinical Terms), the Gene Ontology (for molecular biology), and the Human Phenotype Ontology (for phenotypic abnormalities) and LOINC (Logical observation identifiers names and codes).

Embodiments of the present invention may modify one or more medical ontologies, such as one or more standard medical ontologies (e.g., SNOMED CT), to produce modified medical ontologies within the medical ontologies 112. Embodiments of the present invention may then use such modified medical ontologies in any of the ways disclosed herein in connection with the medical ontologies 112. Such modifying of a medical ontology may include any one or more of the following: adding synonyms of concepts within the ontology to the ontology; removing antonyms of concepts within the ontology from the ontology; and performing post-coordination on the ontology to map concepts within the ontology to terms that a physician or other healthcare worker may use to express such concepts. As one example, "laparoscopic hernia repair" is a concept within the SNOMED ontology. Embodiments of the present invention may generate a modified version of SNOMED which maps a phrase such as "performed a mesh hernia repair by cutting the abdomen" to the SNOMED concept of "laparoscopic hernia repair," so that when the former phrase is observed (e.g., in the existing medical data 102), the system 100 may map that phrase to the SNOMED concept of "laparoscopic hernia repair."

In general, the first semantically-annotated medical data 114 may include data representing one or more concepts extracted from the existing medical data 102. Such concept data in the first semantically-annotated medical data 114 may for example, take the form of markup of the corresponding data from the existing medical data 102. As this implies, the first semantically-annotated medical data 114 may include some or all of the existing medical data 102 in addition to concept data representing concepts extracted from the existing medical data 102. As a particular example, if the existing medical data 102 includes text representing a particular medication, the first semantically-annotated medical data 114 may include the text representing the particular medication and markup of that text representing the particular medication in a computer-processable form (e.g., according to one or more of the medical ontologies 112).

More specifically, the first semantically-annotated medical data 114 is, as its label implies, "semantically annotated." Mere annotation, in contrast to semantic annotation, might involve, for example, adding metadata or labels to the existing medical data 102. For example, annotation of the one or more clinical notes 104*c* may involve marking or highlighting terms in the text and tagging them with their appropriate categories, such as "symptom," "diagnosis," or "medication." This annotation process makes the unstructured text more structured and machine-readable. The NLP engine 110 may perform such annotation, but does more than this when semantically annotating the existing medical data 102 to generate the first semantically-annotated medical data 114. Semantic annotation goes a step further by adding meaning and context to the annotated terms in the first semantically-annotated medical data 114, linking them to concepts within one or more of the medical ontologies 112. This makes the first semantically-annotated medical data 114 not only structured but also interconnected and imbued with deeper meaning. In summary, while non-semantic annotating adds structure to the existing medical data 102, semantic annotating adds context, depth, interconnectedness, and meaning to the existing medical data 102 by linking that data to a broader framework of knowledge represented by one or more of the medical ontologies 112. For example, the annotations in the first semantically-annotated medical data 114 may indicate not only the meanings of individual data elements in the first semantically-annotated medical data 114 but also the relationships of those meanings to meanings of other data elements in the first semantically-annotated medical data 114.

As described above, the NLP engine 110 may apply natural language processing and the medical ontologies 112 to the existing medical data 102 to generate first semantically-annotated medical data 114 associated with the first patient. This may include, for example, performing any one or more of the following on the existing medical data 102:

Entity Recognition: The NLP engine 110 may process the existing medical data 102 to identify terms or phrases that are likely clinically relevant. Using the medical ontologies 112, the NLP engine 110 may for example, recognize text that mentions concepts that are relevant to the disease associated with the disease-specific semantic model 120.

Semantic Mapping: Once entities are identified, the NLP engine 110 may map those entities to their standardized codes within the medical ontologies 112.

Contextual Understanding: The relationships and hierarchy defined in the medical ontologies 112 may help the NLP engine 110 to infer context. For instance, if a clinical note in the existing medical data 102 mentions a specific symptom alongside a breast cancer diagnosis, the NLP engine 110, using the medical ontologies 112, might infer that this symptom is related to the cancer diagnosis.

Data Structuring: Using the medical ontologies 112, the NLP engine 110 may categorize and organize the extracted data into one or more standardized formats.

Operation 204 may include applying NLP using the medical ontologies 112, thereby resulting in data, in the first instance 130*a* of the first disease-specific semantic model 120, which is annotated with a plurality of semantic codes representing concepts in the medical ontologies 112. Applying NLP using the medical ontologies 112 may include marking up the existing medical data 102 with data representing a plurality of concepts. The resulting first semantically-annotated medical data 114 may be or include XML data. Applying NLP using the medical ontologies 112 may include generating, for each of a plurality of data elements in the first semantically-annotated medical data 114, data representing a source of that data element in the existing medical data 102. The system 100 may generate output (e.g., visual output) representing both a data element in the first semantically-annotated medical data 114 and the source of that data element in the existing medical data 102, such as for the purpose of enabling a user of the system 100 to understand and verify the justification for the data element in the first semantically-annotated medical data 114.

As mentioned above, the system 100 may include a plurality of value sets 122. Each such value set may for example, include a specific set of codes and/or terms derived from one or more standard clinical terminologies or coding systems. Each of the value sets 122 may for example, represent a group of clinical concepts that are relevant to a particular corresponding use case or clinical quality measure. For example, one of the value sets 122 might include some or all the codes from different coding systems that relate to breast cancer, while another one of the value sets 122 might group include some or all the codes from different coding systems that relate to diabetes. Such coding systems may include, for example, any one or more of the following: the International Classification of Diseases (ICD), SNOMED CT (Systematized Nomenclature of Medicine Clinical Terms), and the Current Procedural Terminology (CPT). The value sets 122 may provide an organized way to extract, interpret, and standardize specific clinical concepts from unstructured or semi-structured text.

Each of the plurality of data models 124 may be a structured and organized representation of concepts and relationships within a particular domain, in order to facilitate data processing, analysis, and/or storage. Each of the data models 124 may include any one or more of the following, in relation to the particular disease represented by the disease-specific semantic model 120:

Entity Definitions: Identification of key clinical concepts or entities that the NLP engine 110 recognizes, extracts, and/or process. For example, in the clinical notes 104*c*, entities might include diagnoses, symptoms, medications, procedures, and/or lab values.

Relationships: Description of how different entities relate to each other. For instance, a medication might be linked to a specific dosage or a diagnosis might be linked to a particular symptom.

Attributes: Additional details or characteristics about an entity. Using the medication example, attributes might include dosage, frequency, route of administration, and duration.

Constraints: Limitations or conditions applied to entities, relationships, or attributes. For instance, constraints may specify valid value ranges for lab results.

Standards and Terminologies: Mapping or alignment of entities, attributes, and relationships to standard medical terminologies or coding systems, such as SNOMED CT, ICD, CPT, and LOINC.

Annotations: In training datasets for NLP, annotations refer to labeled instances of entities or relationships within the text. A data model may specify what types of annotations are needed, the format, and guidelines for how annotations should be applied.

Different disease-specific models may include different data models, among which any of the above-described elements may differ.

The plurality of rules 126 may include, for example, any one or more of the following kinds of rules:

Validation Rules: These ensure that the data conforms to certain standards or criteria. For instance, a rule might specify that a particular lab value (like blood glucose level) should always be a non-negative number.

Transformation Rules: If data needs to be transformed or converted into a different format or unit, these rules dictate how that process occurs. For example, converting temperatures from Celsius to Fahrenheit.

Association and Dependency Rules: These define how different data entities relate to one another. A rule might state that every prescription must be associated with a specific medication name and dosage.

Derivation Rules: Sometimes, certain data fields or values are derived based on other data. For instance, a rule might dictate that a "diabetes control status" is determined based on a series of Hemoglobin A1c values over a certain time period.

Normalization Rules: These rules may help in mapping extracted entities to standard terminologies or codes. For instance, a normalization rule might map both the concepts of "high blood sugar" and "elevated glucose levels" to a standard code for hyperglycemia.

Temporal Rules: These can help in understanding sequences or time-based patterns in the data. For example, specifying that a certain symptom should occur before a diagnosis is made.

Inference Rules: These are especially common in decision-support systems where certain conclusions or recommendations are made based on the existing data. For instance, if multiple symptoms and a specific lab value are present, infer a particular diagnosis.

Conflict Resolution Rules: In cases where data sources might provide conflicting information, these rules dictate how conflicts are resolved.

Different disease-specific models may include different rules, which may differ from each other in any of a variety of ways.

The reasoning engine 116 may use the plurality of rules 126 to populate the first instance 130a of the first disease-specific semantic model 120 in any of a variety of ways. For example, the plurality of rules 126 may formalize diagnostic criteria, algorithms, and/or guidelines that are used in clinical practice to diagnose the particular disease represented by the disease-specific semantic model 120. For example, if the disease represented by the disease-specific semantic model 120 has clear diagnostic criteria based on measurable factors (e.g., lab results, vital signs, symptom presence/absence), these criteria may be encoded into the plurality of rules 126.

The reasoning engine 116 may for example, apply some or all of the value sets 122, some or all of the plurality of data models 124, and some or all of the plurality of rules 126 to the existing medical data 102 and/or to the first semantically-annotated medical data 114 to generate the first instance 130a of the first disease-specific semantic model 120.

The plurality of rules 126 may for example, combine lower level information (e.g., identified medical concepts from the medical ontologies 112) into higher level concepts (e.g., concepts that do not appear explicitly in the existing medical data 102). As example, in cancer staging, the plurality of rules 126 may when applied to the existing medical data 102 and/or the first semantically-annotated medical data 114, determine the stage of a patient's cancer based on a plurality of concepts, lab results, and other statements found in a plurality of documents in the existing medical data 102, even in those documents do not include any explicit statements about the patient's cancer stage.

Applying the reasoning engine 116 to the first semantically-annotated medical data 114 to generate the first instance 130a of the first disease-specific semantic model 120 may include: using a particular one of the plurality of rules 126 to generate a first data element in the first instance 130a of the first disease-specific semantic model 120; generating data associating the particular one of the plurality of rules 126 with the first data element; and storing the data associating the particular one of the plurality of rules 126 with the first data element in the first instance 130a of the first disease-specific semantic model 120. The system 100 may generate output (e.g., visual output) representing both the first data element and the rule in the plurality of rules 126 that generated the first data element, such as for the purpose of enabling a user of the system 100 to understand and verify the justification for the first data element in the first semantically-annotated medical data 114.

Applying the reasoning engine 116 to the first semantically-annotated medical data 114 to generate the first instance 130a of the first disease-specific semantic model 120 may include using one or more of the plurality of data models 124 to generate the first instance 130a of the first disease-specific semantic model 120. Each of the plurality of data models 124 may for example, define a set of target data elements with associated permissible value ranges which, when instantiated (e.g., in the first instance 130a of the first disease-specific semantic model 120), generate an instance of the disease-specific semantic model 120 for a given patient. More generally, each of the plurality of data models 124 may for example, encode a domain expert's knowledge about the disease associated with the disease-specific semantic model 120 in a way that the reasoning engine 116 can use to automatically identify the most essential pieces of information about the patient (e.g., the patient's disease stage).

Applying the reasoning engine 116 may include any one or more of the following:

identifying an inconsistency between at least two data elements in the existing medical data 102 or the first semantically-annotated medical data 114, resolving the inconsistency, and storing data based on the resolution in the first instance 130a of the first disease-specific semantic model 120;

identifying a temporal trend in the existing medical data 102 or the first semantically-annotated medical data 114 and storing data representing the temporal trend in the first instance 130a of the first disease-specific semantic model 120;

drawing a medical conclusion about the first patient based on the existing medical data 102 or the first semantically-annotated medical data 114 and storing data representing the medical conclusion in the first instance 130a of the first disease-specific semantic model 120.

Drawing a medical conclusion about the first patient based on the existing medical data 102 may include, for example: identifying, in the first semantically-annotated medical data 114, a plurality of data elements representing at least one medical condition; drawing the medical conclusion about the first patient based on the plurality of data elements; and storing the data representing the medical conclusion in the first instance 130a of the first disease-specific semantic model 120, wherein the data representing the medical conclusion is not in the first semantically-annotated medical data 114. As a particular example, if the first semantically-annotated medical data 114 contains data indicating the presence of signs and symptoms of fever in the first patient, the presence of infiltrates on an X-ray of the first patient, and evidence of a micro-organism in a sputum lab test of the first patient, the reasoning engine 116 may draw the medical conclusion that the first patient has pneumonia, even though neither the existing medical data 102 nor the first semantically-annotated medical data 114 includes any data explicitly indicating that the first patient has pneumonia. Instead, it is only as a result of the reasoning performed by the reasoning engine 116 that the first patient's pneumonia is identified and that data representing that pneumonia is stored in the first instance 130a of the first disease-specific semantic model 120.

When the reasoning engine 116 stores any data element in the first instance 130a of the first disease-specific semantic model 120, such as any of the data elements described above (e.g., a data element representing a resolved inconsistency, a temporal trend, or a medical conclusion), the reasoning engine 116 may also store, in the first instance 130a of the first disease-specific semantic model 120, data representing an association between that data element and either or both of the following: data in the existing medical data 102 that is the source of the data element, and one or more of the plurality of rules 126 that were used to generate that data element.

The first instance 130a of the first disease-specific semantic model 120 may include data explicitly representing a medical condition of the first patient, even if the existing medical data 102 does not include data explicitly representing the medical condition of the first patient. For example, the first instance 130a of the first disease-specific semantic model 120 may include data explicitly indicating that the first patient has breast cancer (or otherwise satisfies clinical criteria for breast cancer), even if the existing medical data 102 does not include any data explicitly indicating that the first patient has breast cancer (or otherwise satisfies clinical criteria for breast cancer). Similarly, the first instance 130a of the first disease-specific semantic model 120 may include data explicitly representing a procedure, medication, adverse reaction, laboratory test, medical history, surgical history, family history, or vital sign of the first patient even if the existing medical data 102 does not include any data explicitly indicating such information about the first patient. As this implies, the reasoning engine module 118 may infer the medical condition or other information about the first patient from the existing medical data 102.

As mentioned above, the system 100 may generate and store additional disease-specific semantic models, representing additional disease, and may generate and store instances of such disease-specific models for the first patient and for other patients. For example, if the system includes a second disease-specific semantic model that represents a different disease than the disease-specific semantic model 120, the system 100 may use the NLP engine 110 to apply natural language processing to the existing medical data 102 to generate second semantically-annotated medical data associated with the first patient; and to apply the reasoning engine 116 to the second semantically-annotated medical data to generate a first instance of the second disease-specific semantic model. When the reasoning engine 116 generates the first instance of the second disease-specific semantic model, the reasoning engine 116 may:

apply the same value sets 122 as when generating the first instance 130a of the first disease-specific semantic model 120 or different value sets;

apply the same plurality of data models 124 as when generating the first instance 130a of the first disease-specific semantic model 120 or different data models; or apply the same plurality of rules 126 as when generating the first instance 130a of the first disease-specific semantic model 120 or a different plurality of rules.

The system 100 may modify the first instance 130a of the first disease-specific semantic model 120 in any of a variety of ways and in response to any of a variety of triggering events. Any modification disclosed herein the first instance 130a of the first disease-specific semantic model 120 may result in the modifications replacing the original data in the first instance 130a of the first disease-specific semantic model 120 or in the modifications supplementing the original data in the first instance 130a of the first disease-specific semantic model 120. For example, if the system 100 modifies a first version of the first instance 130a of the first disease-specific semantic model 120 to produce a second version of the first instance 130a of the first disease-specific semantic model 120, the system 100 may either replace the first version with the second version or supplement the first version with the second version. In the latter case, the result may be that the first instance 130a of the first disease-specific semantic model 120 includes both the first and second versions of the first instance 130a of the first disease-specific semantic model 120. In this way, the system 100 may store a history of versions of the first disease-specific semantic model 120 over time.

The system 100 may generate a new version of the first instance 130a of the first disease-specific semantic model 120 based on any one or more of the following:

Updates to the existing medical data 102: For example, if data elements are added to, deleted from, or modified within the existing medical data 102, the system 100 may use any of the techniques disclosed herein to generate a new version of the first instance 130a of the first disease-specific semantic model 120 based on the updated existing medical data 102.

Updates to the data ingestion and NLP module 108: The data ingestion and NLP module 108 may be updated in any of a variety of ways. For example, one or more improvements, corrections, or additions may be made to the NLP model in the NLP engine 110, such as to cover instances that were not detected or incorrectly annotated by previous versions of the NLP model. As another example, one or more new NLP models may be added to the NLP engine 110, such as because a new/updated medical ontology is being introduced. As yet another example, one or more new NLP models may be added to the NLP engine 110, such as because a new/updated disease-specific model is being developed and the existing NLP models in the NLP engine 110 do not cover the required concepts. In any of these cases, the system 100 may use any of the techniques disclosed herein to generate a new version of the first instance 130a of the first disease-specific semantic model 120 based on the updated data ingestion and NLP module 108.

Updates to the medical ontologies 112: For example, if a new medical ontology is added to the medical ontologies 112 or any change is made to any of the existing medical ontologies 112, the system 100 may use any of the techniques disclosed herein to generate a new version of the first instance 130a of the first disease-specific semantic model 120 based on the updated medical ontologies 112.

Updates to the plurality of data models 124: For example, if a new data model is added to the plurality of data models 124 or any change is made to any of the existing plurality of data models 124, the system 100 may use any of the techniques disclosed herein to generate a new version of the first instance 130a of the first disease-specific semantic model 120 based on the updated plurality of data models 124. Examples of ways in which disease-specific models may change over time include changes based on changes to evidence-based practices. For example, a disease-specific model may change to reflect a change in the criteria that a tumor must satisfy in order to qualify as "stage 3." As another example, the system 100 may modify a disease-specific model in response to feedback received from one or more users of the system 100 in any of the ways disclosed herein.

Updates to the plurality of rules 126: For example, if a new rule is added to the plurality of rules 126 or any change is made to any of the existing plurality of rules 126, the system 100 may use any of the techniques disclosed herein to generate a new version of the first instance 130a of the first disease-specific semantic model 120 based on the updated plurality of rules 126.

Updates to the plurality of value sets 122: For example, if a new rule is added to the plurality of value sets 122 or any change is made to any of the existing plurality of value sets 122, the system 100 may use any of the techniques disclosed herein to generate a new version of the first instance 130a of the first disease-specific semantic model 120 based on the updated plurality of value sets 122.

The system may generate a new version of the first instance 130a of the first disease-specific semantic model 120 in response to any of a variety of triggering events, such as automatically in response to any of the updates above or in response to input from a user of the system 100 requesting that such a new version be generated.

Figure 3:
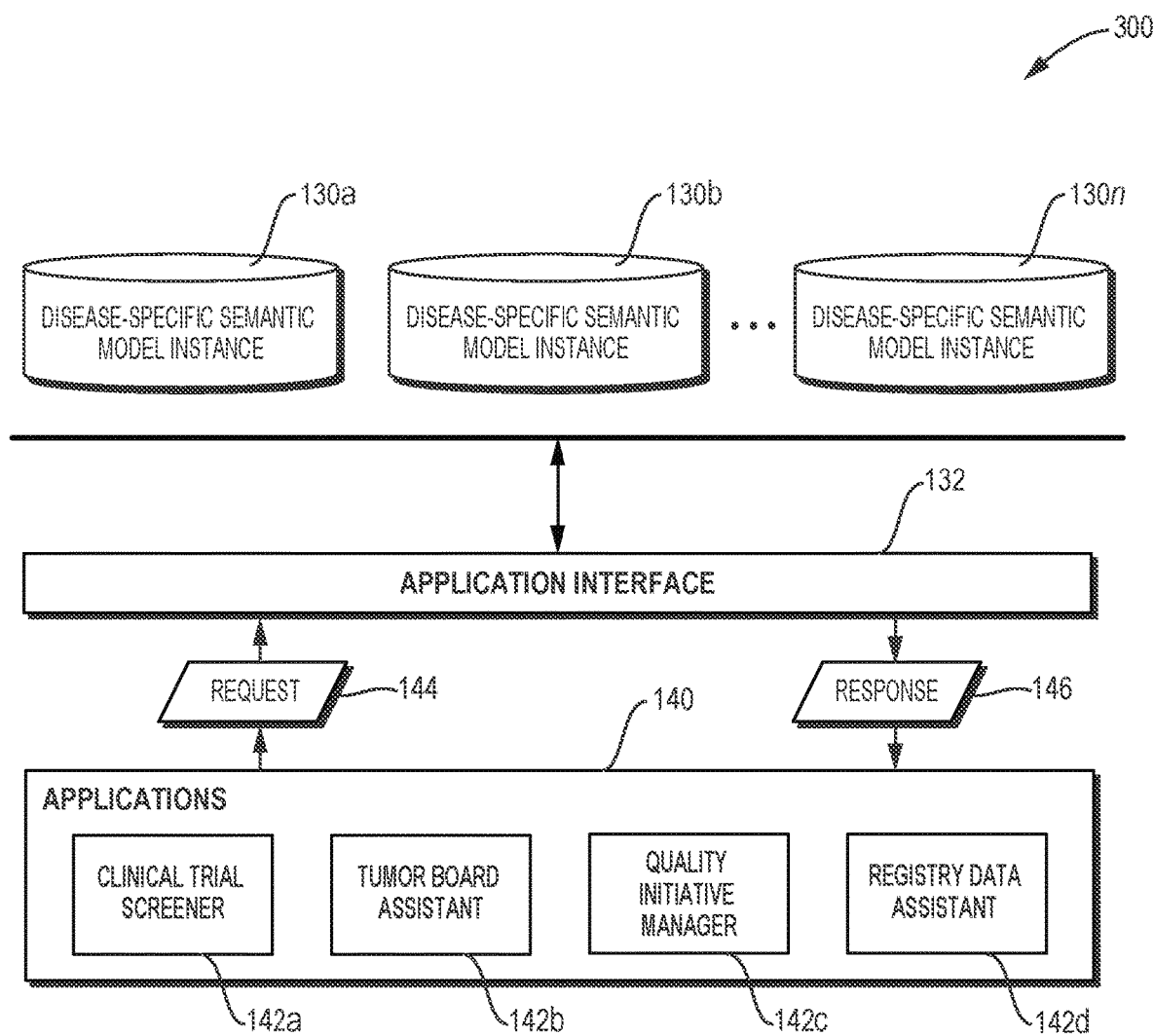
FIG. 3 is a dataflow diagram of a system for extracting information from an instance of a disease-specific semantic model according to one embodiment of the present invention.
Figure 4:
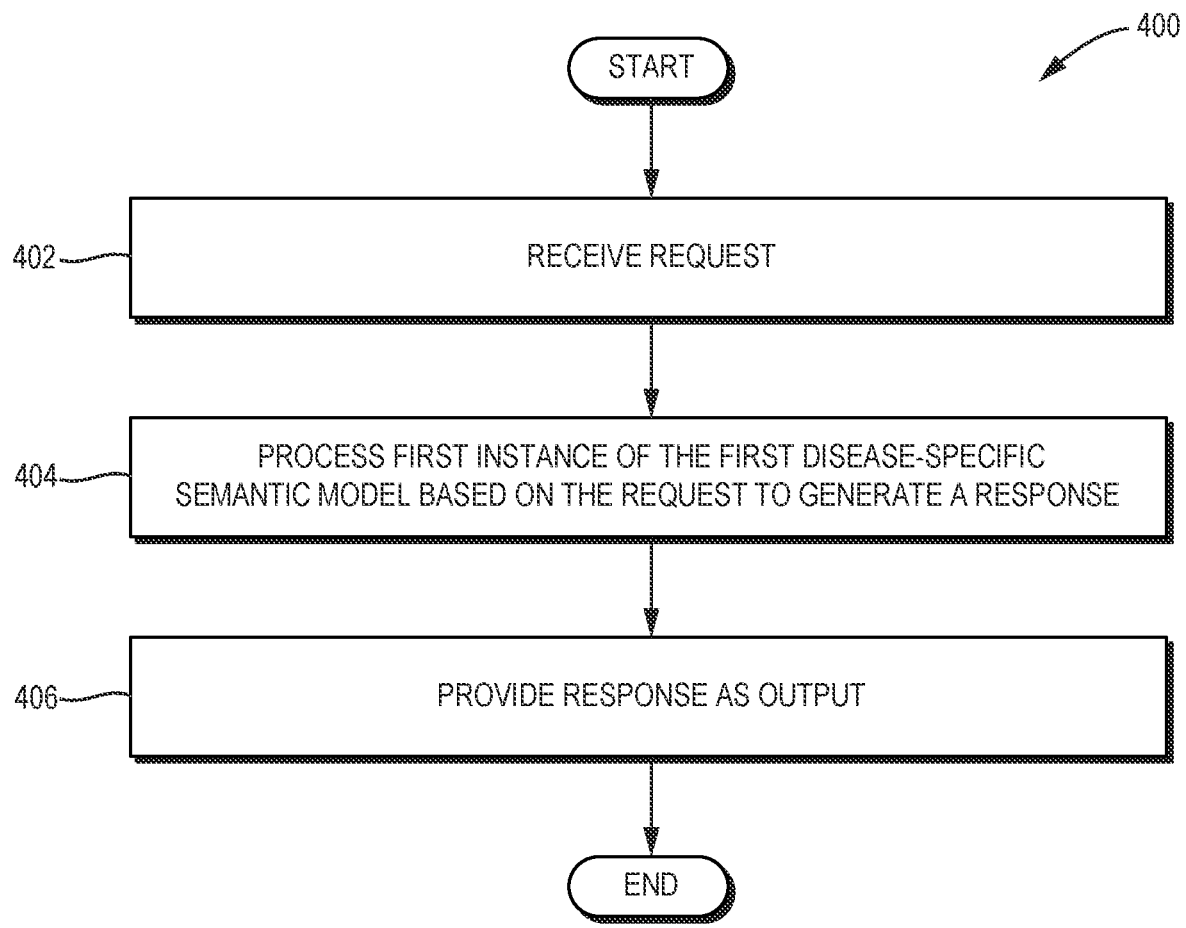
FIG. 4 is a flowchart of a method performed by the system of FIG. 3 according to one embodiment of the present invention.

Referring to FIG. 3, a dataflow diagram is shown of a system 300 for extracting information from any one or more of a plurality of instances 130a-n of the first disease-specific semantic model 120 according to one embodiment of the present invention. Referring to FIG. 4, a flowchart is shown of a method 400 performed by the system 300 of FIG. 3 according to one embodiment of the present invention. Although the description below may refer to first instance 130a in connection with FIGS. 3 and 4, it should be understood that the system 300 of FIG. 3 and the method 400 of FIG. 4 maybe applied to any one or more of the plurality of instances 130a-n, either individually or in any combination. For example, any instance of the request 144 may be applied to any single one of the plurality of instances 130a-n or to some or all of the plurality of instances 130a-n collectively.

The system 300 may include an application interface 132, which may receive input from and provide output to one or more external systems, such as one or more applications 140. Merely as examples, the applications 140 in the embodiment shown in FIG. 1 include a clinical trial screener application 142a, a tumor board assistant application 142b, and a quality initiative manager application 142c, and a registry data assistant application 142d. More generally, the application interface 132 may receive input from and provide output to any kind of hardware and/or software system. Therefore, although the application interface 132 is referred to herein as an "application" interface, more generally the application interface 132 may be an interface to any kind of system, whether or not an application.

For example, the application interface 132 may receive a request 144 (FIG. 4, operation 402); process the first instance 130a of the first disease-specific semantic model 120 based on the request 144 to generate a first processed instance of the first disease-specific semantic model (also referred to herein as a response 146) (FIG. 4, operation 404); and providing the response 146 as output (FIG. 4, operation 406). The request 144 may for example, contain data representing a request to query, summarize, or perform any other kind of processing on the first instance 130a of the first disease-specific semantic model 120 to generate the response 146. For example, if the request 144 includes a query, the application interface 132 may query the first instance 130a of the first disease-specific semantic model 120 to generate a query result, and provide the query result as the response 146.

As another example, the request 144 may include data representing a request to summarize the first instance 130a of the first disease-specific semantic model 120, in response to which the application interface 132 may summarize the first instance 130a of the first disease-specific semantic model 120 to generate the response 146, which may include a summary of the first instance 130a of the first disease-specific semantic model 120. Such summarizing may include, for example, reducing and/or projecting information in the first instance 130a of the first disease-specific semantic model 120 into a more condensed form for the purpose of focusing a user's attention on only relevant information within the response 146. As this implies, the request 144 may include information that is lacking in the response 146.

When summarizing the first instance 130a of the first disease-specific semantic model 120 to include only relevant information in the response 146 (or to exclude irrelevant information from the first instance 130a in the response 146), the application interface 132 may use any of a variety of measures of relevance (also referred to herein as "relevance criteria"). For example, the application interface 132 may use a measure of relevance which causes the application interface 132 to include, in the response 146, only information that is clinically relevant to a particular user (e.g., physician), a particular attribute or other aspect of the first instance 130a (such as a stage of a medical condition of the first patient), or a particular time (e.g., the current time).

For example, the response 146 may include data that represents a clinical interpretation of data in the first instance 130a of the first disease-specific semantic model 120 at a particular time (e.g., the current time), based on some relevance criterion. As this implies, the patient status may not include data from the first instance 130a of the first disease-specific semantic model 120 from a previous time that is not relevant at a particular time, as determined based on a particular relevance criterion. For example, if the first instance 130a of the first disease-specific semantic model 120 contains data indicating that the first patient's had an ECOG of 3 two years ago, an ECOG of 1 one year ago, and an ECOG of 0 today, the application interface 132 may include only the ECOG of 0 in the response 146 based on a particular relevance criterion because, according to that relevance criterion, only the ECOG of 0 (and not the previous ECOGs of 3 and 1) are relevant.

Although, in the example just provided, the most recent data from the first instance 130a was selected for inclusion in the response 146 (summary), this is merely an example. Some other relevance criterion might result in the application interface 132 selecting data from a previous time (e.g., the patient's ECOG of 3) for inclusion in the response 146, and not data from a more recent time. More generally, the application interface 132 may use the relevance criterion to select the most clinically relevant data for inclusion in the response 146.

As another example, and as will be described in more detail below, a relevance criterion may be associated with a particular one of the applications 140, and different ones of the applications 140 may be associated with different relevance criteria. For example, the clinical trial screener 142*a* may be associated with a first relevance criterion, while the tumor board assistant application 142*b* may be associated with a second relevance criterion, where the first relevance criterion may differ from the second relevance criterion. When the application interface 132 processes a request from a particular application to generate a summary of the first instance 130*a* of the first disease-specific semantic model 120, the application interface 132 may identify the relevance criteria associated with the requesting application and apply that relevance criteria when generating the summary of the first instance 130*a* of the first disease-specific semantic model 120. As this implies, the summaries that the application interface 132 generates based on the same first instance 130*a* of the first disease-specific semantic model 120 may differ depending on which of the applications 140 requested the summary, due to differences in relevance criteria among the applications 140.

Examples of types of summarization that the application interface 132 may use include extractive summarization, abstractive summarization, query-based summarization, thematic summarization, and user-specific summarization. The application interface 132 may use one or more measures of relevance to perform such summarizing, such as one or more measures of relevance received via manual input from a user and/or one or more measures of relevance generated automatically by the system 100, such as based on one or more characteristics of the requesting application and/or a requesting user (e.g., physician).

In the case of user-specific summarization, the application interface 132 may summarize the first instance 130*a* of the first disease-specific semantic model 120 to generate the response 146 based on one or more characteristics of a user, such as a physician or other healthcare worker. Such characteristics may include, for example, one or more of the user's: specialty or subspecialty, experience level, preferred language/terminology, role, historical interactions, type of decision being made, patient load, technological proficiency, affiliated institution/network, and geographic location. As a particular example, when summarizing for a cardiologist, the application interface 132 may summarize the first instance 130*a* of the first disease-specific semantic model 120 to highlight heart-related issues, medications related to cardiovascular health, and relevant test results, such as ECG or cholesterol levels. In contrast, when summarizing for a radiologist, the application interface 132 may prioritize imaging results, historical comparisons, and related diagnostic notes.

Similarly, the application interface 132 may rephrase some or all of the first instance 130*a* of the first disease-specific semantic model 120 to generate the response 146. Such rephrasing may include rewording some or all of the first instance 130*a* of the first disease-specific semantic model 120 to produce text that is worded differently than the original text, while preserving its overall meaning. Rephrasing may for example, include simplifying complex language, adjusting the tone of language, and/or tailoring text to suit the audience's background or expertise. Rephrasing may include, for example, applying any one or more of the following to the first instance 130*a* of the first disease-specific semantic model 120: simplifying, adjusting the level of formality, changing active voice to passive voice (or vice versa), and performing specialized rephrasing based on one or more characteristics of a user (e.g., physician or other healthcare worker). For example, when rephrasing for a cardiologist, the application interface 132 may rephrase "The patient has a problem with a heart valve" as "The patient exhibits mitral valve prolapse."

Regardless of the process that the application interface 132 uses to generate the response 146, the application interface 132 may generate an initial version of the response 146 using any of the techniques disclosed herein, and then further process that initial version of the response (such as by using a Large Language Model (LLM)) to generate a revised version of the response 146 that is in a more suitable form for output to a user of the system 100. The application interface 132 may output the initial version of the response 146, the revised version of the response 146, or both.

As the above implies, the application interface 132 may generate multiple instances of the response 146 (e.g., multiple summaries/rephrasings) which may differ from each other, such as due to differences in characteristics of the users that are used to generate the multiple instances of the response 146. Furthermore, although the response 146 is shown in FIG. 1 as being generated in response to the request 144, the application interface 132 may generate one or more instances of the response 146 in response to one or more internal triggers, i.e., without receiving and not in response to any external request.

As described above, the disease-specific semantic model module 106 may generate a new version of the first instance 130*a* of the first disease-specific semantic model 120. Any such new version is an example of a second instance 130*b* of the first disease-specific semantic model 120. As another example, the second instance 130*b* of the first disease-specific semantic model 120 may be an instance of the first disease-specific semantic model 120 that the disease-specific semantic model module 106 generated for a second patient by applying any of the techniques disclosed herein to original medical data of the second patient. The first instance 130*a* of the first disease-specific semantic model 120 may differ from the second instance 130*b* of the first disease-specific semantic model 120 in any of a variety of ways.

Figure 5:
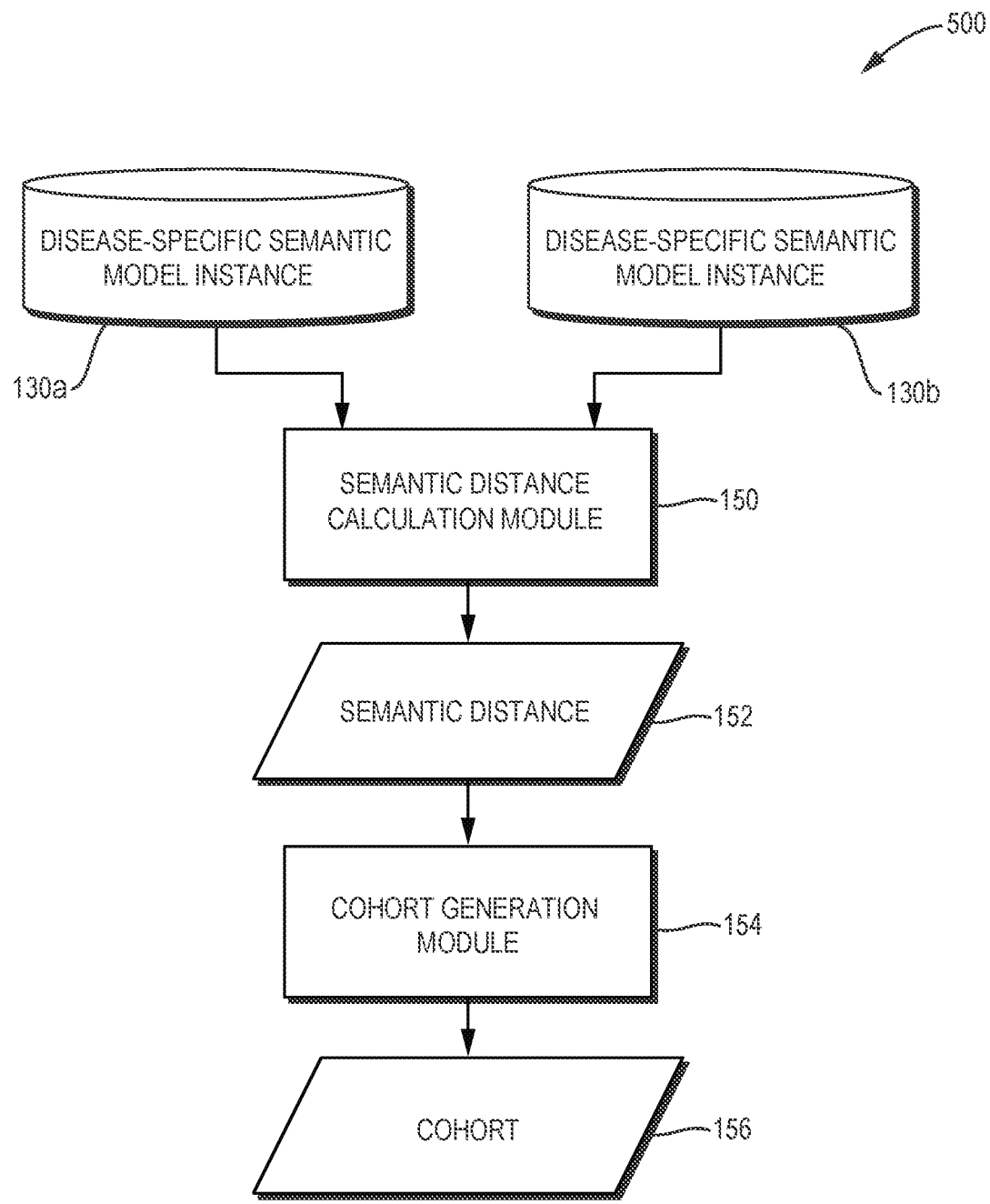
FIG. 5 is a dataflow diagram of a system for calculating semantic distances between disease-specific model instances, and between disease-specific model instances and criteria according to one embodiment of the present invention.
Figure 6:
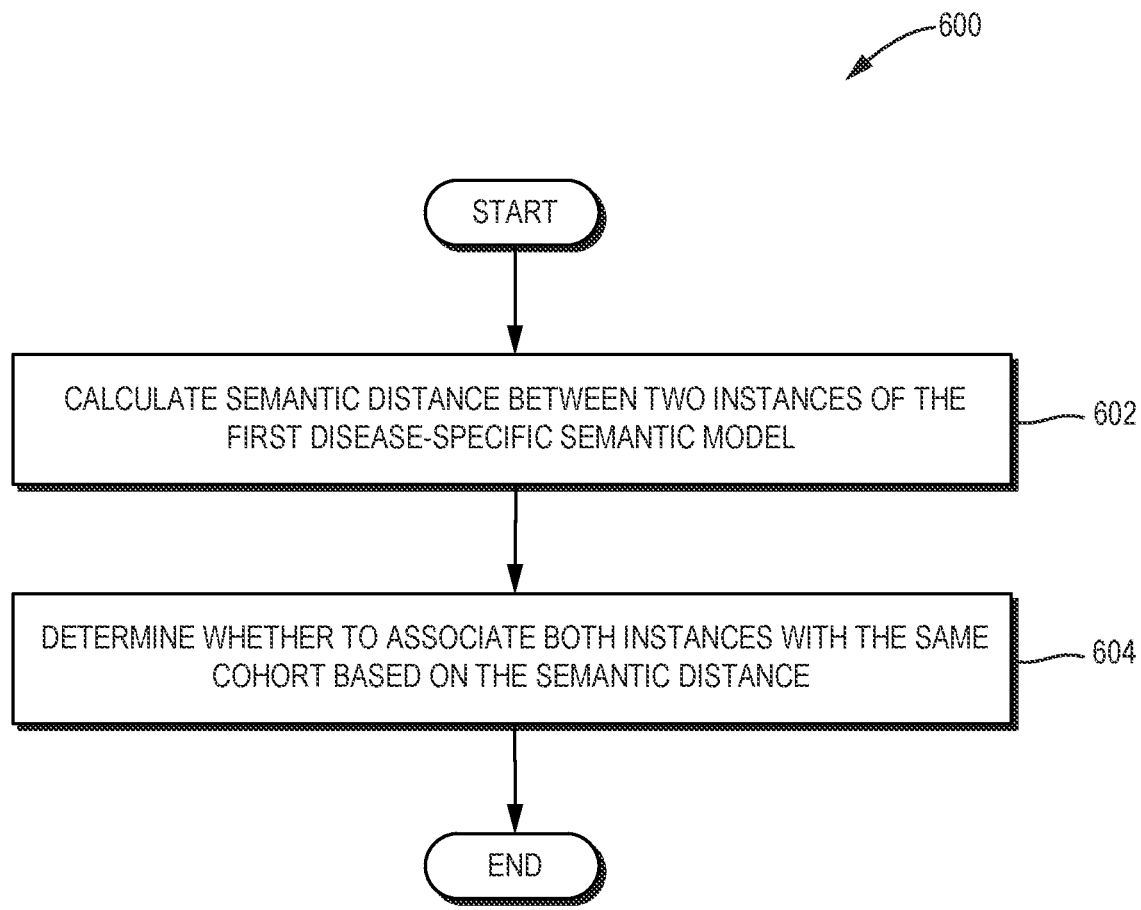
FIG. 6 is a flowchart of a method performed by the system of FIG. 5 according to one embodiment of the present invention.

Referring to FIG. 5, a dataflow diagram is shown of a system 500 for calculating semantic distances between disease-specific model instances, and between disease-specific model instances and criteria, according to one embodiment of the present invention. Referring to FIG. 6, a flowchart is shown of a method 600 performed by the system 500 according to one embodiment of the present invention. The system 500 includes a semantic distance calculation module 150, which may receive the first instance 130*a* of the first disease-specific semantic model 120 and the second instance 130*b* of the first disease-specific semantic model 120 as inputs and calculate a semantic distance between the first instance 130*a* of the first disease-specific semantic model 120 and the second instance 130*b* of the first disease-specific semantic model 120, thereby generating the semantic distance 152 as output (FIG. 6, operation 602).

More generally, and although not shown in FIG. 5, the semantic distance calculation module 150 may calculate a semantic distance not only between two disease-specific model instances, but also between a disease-specific model instance (e.g., the first instance 130*a* or the second instance 130*b*) and a set of criteria (e.g., a set of clinical trial criteria). Examples of this are described below in connection with the system 700 of FIG. 7 and the method 800 of FIG. 8. As yet another example, consider two or more cohorts, each of which includes a plurality of patients (where different cohorts may include different patients, with or without overlap). The semantic distance calculation module 150 may calculate a semantic distance between any one or more pairs of such cohorts.

Although the semantic distance calculation module 150 may calculate the semantic distance 152 in any of a variety of ways, in general the semantic distance calculation module 150 may calculate the semantic distance 152 to represent a measure of difference or similarity in meaning between the inputs to the semantic distance calculation module 150, such as may be inferred from those inputs' structural annotations (e.g., as generated by the NLP engine 110 in the first semantically-annotated medical data 114) and/or semantic annotations (e.g., as generated by the reasoning engine module 118 in the first instance 130a and/or the second instance 130b). As described elsewhere herein, the medical ontologies 112 may provide information about the meaning and context of terms within the inputs to the semantic distance calculation module 150, and the semantic distance calculation module 150 may make use of such meaning and context to calculate the semantic distance 152 between the semantic distance calculation module 150's inputs.

The semantic distance calculation module 150 may use any of a variety of techniques to calculate the semantic distance 152, such as any one or more of the following, in any combination: path length-based measures (which calculate the distance between two concepts based on the number of edges ("hops") between them in an ontology or taxonomy); information content-based measures (which gauge semantic similarity (inverse of distance) based on the information content (IC) of the least common subsumer (LCS) of two concepts); vector space models (in which words or concepts are represented as vectors in a multi-dimensional space, and distance is calculated using measures such as cosine similarity or Euclidean distance); distributional semantic models (which are based on the premise that words with similar meanings appear in similar contexts, and which represent words as vectors derived from their distribution in large corpora); graph-based measures (in which concepts and their relationships may be represented as graphs, with semantic distance calculated based on graph traversal algorithms or measures such as graph connectivity); ontology-based measures (in which ontologies such as SNOMED CT may be used to measure semantic distance); and transformer-based methods (in which models such as GPT, BERT, or their derivatives, which offer contextualized embeddings, may be used to calculate semantic distance by, for example, calculating pairwise distances between such embeddings).

The semantic distance calculation module 150 may for example, use a difference measure of semantic distance to calculate the semantic distance 152, depending on the source of the request for the semantic distance 152. For example, the semantic distance calculation module 150 may use a different measure of semantic distance to calculate the semantic distance 152, depending on which of the applications 140 requests the semantic distance 152. As this implies, the semantic distance calculation module 150 may for example, use a first measure of semantic distance to calculate the semantic distance 152 if a first one of the applications 140 (e.g., the clinical trial screener application 142a) requests the semantic distance 152, and use a second measure of semantic distance to calculate the semantic distance 152 if a second one of the applications 140 (e.g., the tumor board assistant application 142b) requests the semantic distance 152, where the first measure may differ from the second measure.

More generally, the semantic distance calculation module 150 may select and apply different measures of semantic distance when calculating the semantic distance 152, based on one or more characteristics of the request for the semantic distance. As this implies the semantic distance calculation module 150 may apply different measures of semantic distance when calculating the semantic distance 152 in response to requests having characteristics that differ from each other. As a particular example, in the case of clinical trial screening described below in connection with FIGS. 7 and 8, the semantic distance calculation module 150 may use a first measure of semantic distance when calculating a semantic distance between a patient and a first set of clinical trial criteria, and use a second measure (which differs from the first measure) of semantic distance when calculating a semantic distance between the patient and a second set of clinical trial criteria (which differs from the first set of clinical trial criteria). This examples illustrates how embodiments of the present invention may apply different measures of semantic distance when calculating semantic distances to perform clinical trial screening for different clinical trials having different clinical trial criteria.

Although only the single semantic distance 152 is shown in FIG. 5 for ease of illustration, the semantic distance calculation module 150 may calculate any number of semantic distances for its inputs, such as by using different measures of semantic distance to generate multiple outputs for the same inputs. As another example, the semantic distance calculation module 150 may calculate a distance semantic distance for each of a plurality of pairs of inputs, as will be described in more detail below.

The system 500 may include a cohort generation module 154, which may determine, based on the semantic distance 152 between the first instance first instance 130a of the first disease-specific semantic model 120 and the second instance 130b of the first disease-specific semantic model 120, whether to associate the first instance 130a of the first disease-specific semantic model 120 and the second instance 130b of the first disease-specific semantic model 120 with a first patient cohort 156 (FIG. 6, operation 604). Such a determination may be made in any of a variety of ways, such as by determining whether the semantic distance 152 satisfies a particular criterion (e.g., is less than some predetermined threshold) or by clustering a plurality of instances of the first disease-specific semantic model 120 (including the first and second instances 130a and 130b) based on the semantic distances between them, such as by using any of a variety of known clustering techniques. As this implies, although FIGS. 5 and 6 show only two disease-specific semantic module instances 130a-b, the system 500 of FIG. 5 and the method 600 of FIG. 6 maybe applied to any number of model instances to calculate any number of semantic distances between and among such model instances, and to generate any number of cohorts, each of which may include any number of model instances.

Figure 7:
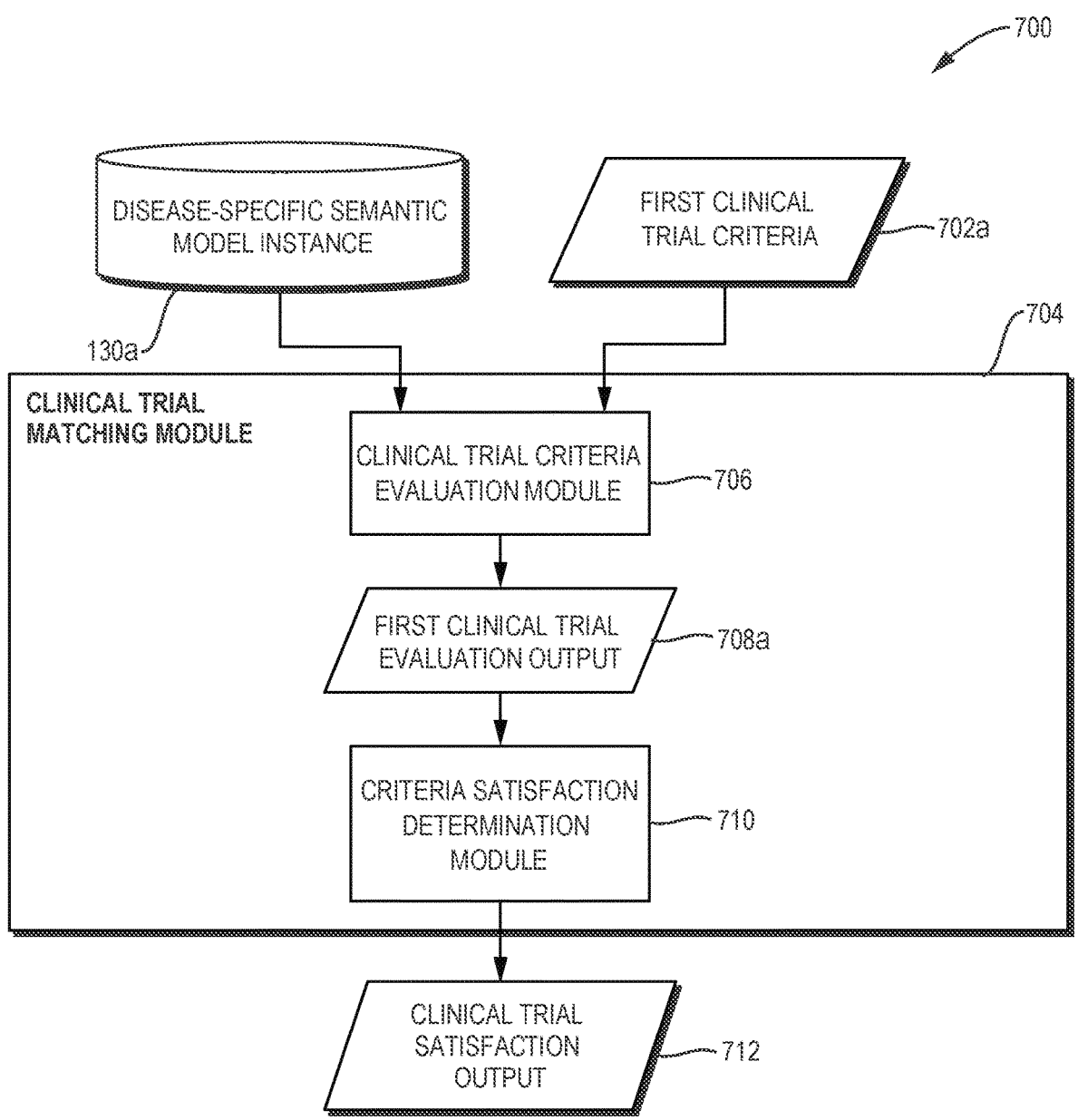
FIG. 7 is a dataflow diagram of a system for performing clinical trial matching according to one embodiment of the present invention.
Figure 8:
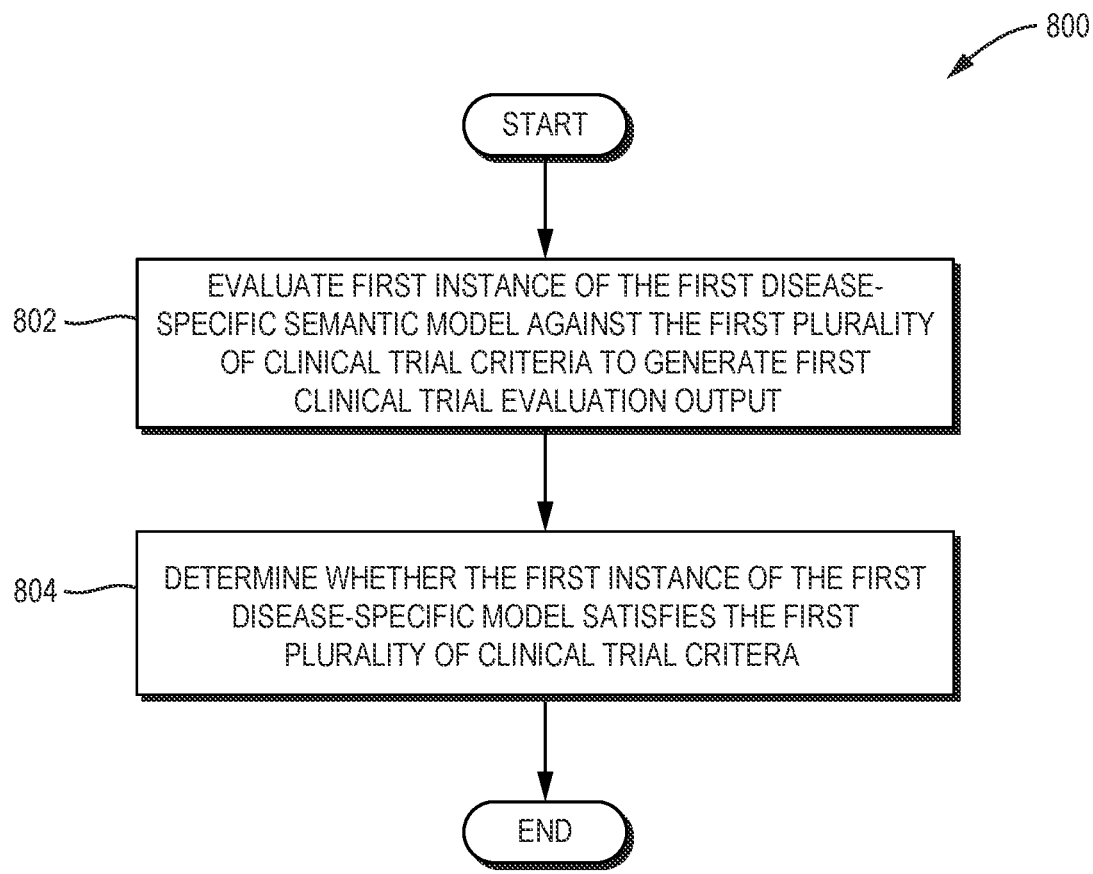
FIG. 8 is a flowchart of a method performed by the system of FIG. 7 according to one embodiment of the present invention.

Referring to FIG. 7, a dataflow diagram is shown of a system 700 for performing clinical trial matching according to one embodiment of the present invention. Referring to FIG. 8, a flowchart is shown of a method 800 performed by the system 700 of FIG. 7 according to one embodiment of the present invention.

For example, the system 700 may determine whether the patient associated with the first instance 130a of the first disease-specific semantic model 120 qualifies for a particular clinical trial, based on a first plurality of criteria 702a associated with the first clinical trial. The first plurality of criteria 702a may for example, include one or more inclusion criteria and/or one or more exclusion criteria associated with the first clinical trial.

The system 700 may include a clinical trial matching module 704. The clinical trial matching module 704 may include a clinical trial criteria evaluation module 706, which may evaluate the first instance 130a of the first disease-specific semantic model 120 against the first plurality of criteria 702a associated with the first clinical trial, thereby generating first clinical trial evaluation output 708a (FIG. 8, operation 802). The evaluation performed by the clinical trial matching module 704 in operation 802 may for example, include calculating a semantic distance between the first instance 130a of the first disease-specific semantic model 120 and the first plurality of criteria 702a associated with the first clinical trial, such as in any of the ways disclosed herein in connection with the semantic distance calculation module 150 of FIG. 5 and the operation 602 of FIG. 6.

Although the clinical trial criteria evaluation module 706 is shown in FIG. 7 as operating on the first instance 130a of the first disease-specific semantic model 120, the clinical trial criteria evaluation module 706 may for example, perform any of a variety of preprocessing on the first instance 130a and then perform operation 802 on the result of such preprocessing. As one example, the clinical trial criteria evaluation module 706 may use any of the techniques disclosed herein (e.g., any of the techniques disclosed herein in connection with FIGS. 4 and 5) to process the first instance 130a of the first disease-specific semantic model 120 to generate the response 146, and the clinical trial criteria evaluation module 706 may then perform operation 802 on the response 146, either instead of or in addition to the first instance 130a itself. As one particular example, the clinical trial criteria evaluation module 706 may summarize the first instance 130a in any of the ways disclosed herein to generate a summary of the first instance 130a, and then perform operation 802 on the summary, either instead of or in addition to the first instance 130a itself.

Such preprocessing (e.g., summarization) may for example, be specific to the clinical trial associated with the first plurality of criteria 702a. For example, the first plurality of criteria 702a may be associated with a corresponding request of the kind shown in FIG. 3, which specifies features of the summarization to be performed in connection with the first plurality of criteria 702a. When summarizing the first instance 130a in operation 802, the clinical trial criteria evaluation module 706 may identify the particular request (e.g., relevance criteria) associated with the first plurality of criteria 702a, and summarize the first instance 130a using the identified request. As this implies, different clinical trials may be associated with different clinical trial criteria and different requests (e.g., relevance criteria), which implies in turn that the clinical trial criteria evaluation module 706 may preprocess disease-specific model instances (e.g., the first instance 130a) differently in connection with different clinical trial criteria in operation 802, thereby resulting in different summaries even of the same first instance 130a of the first disease-specific semantic model 120 for use in matching that first instance 130a against different clinical trial criteria.

The clinical trial matching module 704 may include a criteria satisfaction determination module 710, which may determine, based on the first clinical trial evaluation output 708a, whether the first instance 130a of the first disease-specific semantic model 120 satisfies the first plurality of criteria 702a associated with the first clinical trial, and generate clinical trial satisfaction output 712 representing the result of that determination (FIG. 8, operation 804).

The clinical trial satisfaction output 712 may take any of a variety of forms and may for example, include a binary value (e.g., true or false) and/or a confidence value representing a confidence that the binary value is accurate. As another example, the clinical trial satisfaction output 712 may be or include a score having one of a plurality of permissible values (where the number of permissible values is greater than two), such as a continuous score (e.g., between 0 and 1, with 0 representing a certainty of no match, with 1 representing a certainty of a match, and with values in between 0 and 1 representing estimated likelihoods of matching the clinical trial criteria). The system 700 may for example, use such a score to sort candidate patients by their corresponding scores (e.g., from highest to lowest), thereby enabling users of the system 700 to focus their review on those patients who are most likely to be a good fit for the clinical trial criteria, and not to miss patients who might be a close, but not perfect, match for the clinical trial criteria.

Performing the determination in operation 804 may for example, include generating, based on a rule, data representing a conclusion whether the first instance 130a of the first disease-specific semantic model 120 satisfies the plurality of criteria 702a associated with the first clinical trial. The method 800 may store an association between such a rule and the conclusion represented by the clinical trial satisfaction output 712. Such a stored association may be used to trace the conclusion represented by the clinical trial satisfaction output 712 to the rule (or rules) that were used to generate the clinical trial satisfaction output 712.

Performing the determination in operation 804 may for example, include generating, based on a data element (e.g., a data element in the first instance 130a of the first disease-specific semantic model 120), data representing a conclusion whether the first instance 130a of the first disease-specific semantic model 120 satisfies the plurality of criteria 702a associated with the first clinical trial. The method 800 may store an association between such a data element and the conclusion represented by the clinical trial satisfaction output 712. Such a stored association may be used to trace the conclusion represented by the clinical trial satisfaction output 712 to the data element (or data elements) that were used to generate the clinical trial satisfaction output 712.

Any criterion in the first plurality of criteria 702a may for example, describe a concept (e.g., "chronic liver disease") that is not represented, or at least not represented explicitly, in the first semantically-annotated medical data 114 and/or the first instance 130a. For example, such a criterion may not be represented, or at least not represented explicitly, in some or all of the medical ontologies 112. Furthermore, the existing medical data 102 (e.g., the one or more clinical notes 104c) may not describe such a concept, or at least not describe such a concept explicitly. Yet embodiments of the present invention may determine whether the first instance 130a of the first disease-specific semantic model 120 satisfies such a criterion (e.g., an inclusion criterion or an exclusion criterion), such as in any of the following ways.

The clinical trial matching module 704 may for one or more concepts (e.g., chronic liver disease), determine whether the first instance 130a indicates the presence of that concept and/or the absence of that concept, and store data (e.g., in the first instance 130a and/or an instance of the response 146) representing such a presence and/or absence of the concept. The resulting data representing the presence and/or absence of the concept may be generated and stored even if the existing medical data 102, first semantically-annotated medical data 114, and/or first instance 130a does not indicate any data representing such a concept explicitly. As one example, the resulting data representing the presence and/or absence of the concept may represent that concept even if the medical ontologies 112 do not include any explicit representation of that concept.

Figure 9F:
FIG. 9F illustrates an embodiment of the present invention which determines whether a patent-specific instance of a disease-specific semantic model indicates the presence and/or absence of a particular concept.

The clinical trial matching module 704 may determine whether the first instance 130*a* indicates the presence and/or absence of a particular concept in any of a variety of ways. For example, the clinical trial matching module 704 may apply one or more rules and/or value sets associated with the concept to the first instance 130*a* to determine whether the first instance 130*a* indicates the presence and/or absence of the particular concept. FIG. 9D shows an example in the case of chronic liver disease. In the system 950 of FIG. 9F, there is a chronic liver disease value set 952 and a liver function test value set 954. The system 950 also includes a rule 956 for generating a flag if the first instance 130*a* of the first disease-specific semantic model 120 does not include evidence of chronic liver disease. If the first instance 130*a* of the first disease-specific semantic model 120 does not include any evidence of chronic liver disease, then the reasoning engine module 118 may based on the value sets 952 and 954, the rule 956, and the data in the first instance 130*a* of the first disease-specific semantic model 120, generate a flag which indicates the absence of evidence of chronic liver disease in the first instance 130*a* of the first disease-specific semantic model 120.

As the above description implies, the clinical trial matching module 704 may determine that the first instance 130*a* does not indicate the presence of a particular concept by, for example, using any of the techniques disclosed herein to determine whether the 130*a* does indicate the presence of the particular concept and, if that determination, does not conclude that the first instance 130*a* indicates the present of the particular concept, concluding that the first instance 130*a* does not indicate the presence of the particular concept. For example, if the clinical trial matching module 704 determines whether first instance 130*a* indicates the presence of the particular concept by searching for an instance of particular data in the first instance 130*a*, and the clinical trial matching module 704 does not find any instance of that particular data in the first instance 130*a*, then the clinical trial matching module 704 may conclude that the first instance 130*a* does not indicate the presence of the particular concept. As another example, if the clinical trial matching module 704 determines whether first instance 130*a* indicates the presence of the particular concept by applying a rule to the first instance 130*a* to determine whether the first instance 130*a* satisfies a particular criterion, and the application of the rule results in a determination that the first instance 130*a* does not satisfy the particular criterion, then the clinical trial matching module 704 may conclude that the first instance 130*a* does not indicate the presence of the particular concept. As these examples illustrate, the clinical trial matching module 704 may draw a conclusion that the first instance 130*a* does not represent the particular concept based on a lack of data in the first instance 130*a*.

Any one or more conclusions disclosed herein may be used by embodiments of the present invention (e.g., the clinical trial matching module 704) to draw other conclusions. For example, the output(s) of one or more rules applied by embodiments of the present invention by may used as input(s) to one or more other rules applied by embodiments of the present invention to perform any of the functions disclosed herein. In this way, embodiments of the present invention may apply higher-level reasoning to draw higher-level conclusions than would otherwise be possible based merely on the raw data in the first semantically-annotated medical data 114 and the first instance 130*a* of the first disease-specific semantic model 120.

Furthermore, the ability of embodiments of the present invention to determine that the first instance 130*a* does not represent particular concepts (e.g., particular medical conditions), and the ability of embodiments of the present invention to apply rules to the concepts that are not present explicitly in the first semantically-annotated medical data 114 (and even to concepts that are not present explicitly in the first instance 130*a*), enables embodiments of the present invention to match clinical trial criteria (e.g., the first plurality of criteria 702*a*) against one or more of the following:

concepts that are not represented explicitly in the first semantically-annotated medical data 114;

concepts that are not output by the NLP engine 110 in the first semantically-annotated medical data 114; and concepts that are not in the first instance 130*a* of the first disease-specific semantic model 120.

The clinical trial matching module 704 may for example, match clinical trial criteria (e.g., the first plurality of criteria 702*a*) against semantically-annotated data (e.g., in the first instance 130*a* and/or data derived therefrom using any of the techniques disclosed herein), rather than merely against raw data in the existing medical data 102 or structurally-annotated data, such as the first semantically-annotated medical data 114 output by the NLP engine 110.

Although only one set of clinical trial criteria 702*a* corresponding to a single clinical trial are shown in FIG. 7 for ease of illustration, in practice the system 700 may include any number of clinical trial criteria corresponding to any number of clinical trials. Such sets of clinical trial criteria may differ from each other in any of a variety of ways. The system 700 may repeat the method 800 for any number of such sets of clinical trial criteria in connection with the same first instance 130*a* of the first disease-specific semantic model 120 to thereby generate a plurality of instances of the clinical trial satisfaction output 712, which may be the same as or differ from each other in any of a variety of ways. For example, the instance of the clinical trial satisfaction output 712 that the system 700 generates for the first plurality of criteria 702*a* in connection with the first patient may differ from the instance of the clinical trial satisfaction output 712 that the system 700 generates for a second plurality of criteria in connection with the first patient. Similarly, the system 700 may repeat the method 800 in connection with instances of a plurality of disease-specific models corresponding to the first patient. More generally, the system 700 may perform the method 800 in connection with any number of instances of any number of disease-specific models in connection with any number of patients. As a particular example, if the 700 includes a plurality of disease-specific models and, for each such disease-specific model, a plurality of instances of that disease specific model for each of a plurality of patients, the system 700 may perform the method 800 for each instance of each disease-specific model in connection with each patient.

Although the system 700 and method 800 are shown as being applied to the first instance 130*a* of the first disease-specific semantic model 120, the system 700 and method 800 may be applied to disease-specific semantic models that differ from the first instance 130*a* of the first disease-specific semantic model 120. For example, the system 700 and method 800 may be applied to disease-specific semantic model instances that were generated in ways other than those disclosed in FIGS. 1-6.

Various embodiments of the present invention, such as the systems 100, 300, 500, and 700, may receive feedback on their output and perform a variety of actions in response to such feedback. For example:

The system 100 may receive feedback on content of the first semantically-annotated medical data 114, such as on structural annotations in the first semantically-annotated medical data 114.

The system 100 may receive feedback on content of the first instance 130*a* of the first disease-specific semantic model 120, such as on semantic annotations within the first instance 130*a* of the first disease-specific semantic model 120.

The system 300 may receive feedback on content of the response 146.

The system 500 may receive feedback on the semantic distance 152.

The system 500 may receive feedback on the content of the first patient cohort 156.

The system 700 may receive feedback on the first clinical trial evaluation output 708*a* and/or the clinical trial satisfaction output 712.

Any such feedback may for example, be received manually from a user. Such feedback may take any of a variety of forms, such as binary input representing approval/disapproval of corresponding content, and/or textual input describing the feedback. Regardless of the source and content of the feedback, embodiments of the present invention may process such feedback to influence future actions performed by such embodiments, such as by applying machine learning to such feedback to influence generation of future semantically-annotated medical data, disease-specific semantic model instances, query responses, semantic distances, and patient cohorts. In this way, embodiments of the present invention may improve over time in response to feedback.

One embodiment of the present invention is directed to a method performed by at least one computer processor executing computer program instructions stored on at least one non-transitory computer-readable medium, the computer program instructions being executable by the at least one computer processor to perform a method on a first instance of a first disease-specific semantic model. The method includes: (A) receiving a first request; (B) processing the first instance of the first disease-specific semantic model based on the first request to generate a first processed instance of the first disease-specific semantic model; and (C) providing the first processed instance of the first disease-specific semantic model as output.

The method may further include: (D) receiving a second request; (E) processing the first instance of the first disease-specific semantic model based on the second request to generate a second processed instance of the first disease-specific semantic model; and (F) providing the second processed instance of the first disease-specific semantic model as output.

The method may further include, in response to a change in the first instance of the first disease-specific semantic model, resulting in a second instance of the first disease-specific semantic model: (G) processing the second instance of the first disease-specific semantic model to generate a second processed instance of the first disease-specific semantic model; and (H) providing the second processed instance of the first disease-specific semantic model as output.

The method may further include: (D) receiving updated medical data associated with the first patient; (E) generating a second instance of the first disease-specific semantic model based on the updated medical data associated with the first patient; (F) processing the second instance of the first disease-specific semantic model to generate a second processed instance of the first disease-specific semantic model; and (G) providing the second processed instance of the first disease-specific semantic model as output.

The method may further include: (D) before (A), using a first instance of a natural language processing engine to generate the first instance of the first disease-specific semantic model; (E) after an update to the first instance of the natural language processing engine which results in a second instance of the natural language processing engine, using the second instance of the natural language processing engine to generate a second instance of the first disease-specific semantic model; (F) processing the second instance of the first disease-specific semantic model to generate a second processed instance of the first disease-specific semantic model; and (G) providing the second processed instance of the first disease-specific semantic model as output.

The method may further include: (D) before (A), using a first instance of a plurality of ontological definitions to generate the first instance of the first disease-specific semantic model; (E) after an update to the first instance of the plurality of ontological definitions which results in a second instance of the plurality of ontological definitions, using the second instance of the plurality of ontological definitions to generate a second instance of the first disease-specific semantic model; (F) processing the second instance of the first disease-specific semantic model to generate a second processed instance of the first disease-specific semantic model; and (G) providing the second processed instance of the first disease-specific semantic model as output.

The method may further include: (D) before (A), using a first instance of a data model to generate the first instance of the first disease-specific semantic model; (E) after an update to the first instance of the data model which results in a second instance of the data model, using the second instance of the data model to generate a second instance of the first disease-specific semantic model; (F) processing the second instance of the first disease-specific semantic model to generate a second processed instance of the first disease-specific semantic model; and (G) providing the second processed instance of the first disease-specific semantic model as output.

The method may further include: (D) before (A), using a first instance of a plurality of rules to generate the first instance of the first disease-specific semantic model; (E) after an update to the first instance of the plurality of rules which results in a second instance of the plurality of rules, using the second instance of the plurality of rules to generate a second instance of the first disease-specific semantic model; (F) processing the second instance of the first disease-specific semantic model to generate a second processed instance of the first disease-specific semantic model; and (G) providing the second processed instance of the first disease-specific semantic model as output.

The method may further include: (D) before (A), using a first instance of a plurality of value sets to generate the first instance of the first disease-specific semantic model; (E) after an update to the first instance of the plurality of value sets which results in a second instance of the plurality of value sets, using the second instance of the plurality of value sets to generate a second instance of the first disease-specific semantic model; (F) processing the second instance of the first disease-specific semantic model to generate a second processed instance of the first disease-specific semantic model; and (G) providing the second processed instance of the first disease-specific semantic model as output.

One embodiment of the present invention is directed to a system including at least one non-transitory computer-readable medium having computer program instructions stored thereon, the computer program instructions being executable by at least one computer processor to perform a method on a first instance of a first disease-specific semantic model. The method includes: (A) receiving a first request; (B) processing the first instance of the first disease-specific semantic model based on the first request to generate a first processed instance of the first disease-specific semantic model; and (C) providing the first processed instance of the first disease-specific semantic model as output.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually For example, embodiments of the present invention use computerized natural language processing to automatically semantically-annotate data, and process such data automatically to generate a semantically-annotated instance of a disease-specific model. Such components are inherently computer-implemented and provide a technical solution to the technical problem of automatically processing data that would otherwise not be processable automatically by a computer to perform functions such as determining whether a patient qualifies for a clinical trial.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

Any step or act disclosed herein as being performed, or capable of being performed, by a computer or other machine, may be performed automatically by a computer or other machine, whether or not explicitly disclosed as such herein. A step or act that is performed automatically is performed solely by a computer or other machine, without human intervention. A step or act that is performed automatically may for example, operate solely on inputs received from a computer or other machine, and not from a human. A step or act that is performed automatically may for example, be initiated by a signal received from a computer or other machine, and not from a human. A step or act that is performed automatically may for example, provide output to a computer or other machine, and not to a human.

The terms "A or B," "at least one of A or/and B," "at least one of A and B," "at least one of A or B," or "one or more of A or/and B" used in the various embodiments of the present disclosure include any and all combinations of words enumerated with it. For example, "A or B," "at least one of A and B" or "at least one of A or B" may mean: (1) including at least one A, (2) including at least one B, (3) including either A or B, or (4) including both at least one A and at least one B.

Although terms such as "optimize" and "optimal" are used herein, in practice, embodiments of the present invention may include methods which produce outputs that are not optimal, or which are not known to be optimal, but which nevertheless are useful. For example, embodiments of the present invention may produce an output which approximates an optimal solution, within some degree of error. As a result, terms herein such as "optimize" and "optimal" should be understood to refer not only to processes which produce optimal outputs, but also processes which produce outputs that approximate an optimal solution, within some degree of error.

What is claimed is:

1. A method performed by at least one computer processor executing computer program instructions stored on at least one non-transitory computer-readable medium, the computer program instructions being executable by the at least one computer processor to perform the method, the method comprising:
   (A) receiving first original medical data associated with a first patient over time;
   (B) generating, based on the first original medical data, first semantically annotated medical data associated with the first patient, comprising applying a Natural Language Processing (NLP) engine that uses at least one medical ontology to generate the first semantically annotated medical data based on the first original medical data, wherein applying the NLP engine to the first medical data comprises applying rules to at least some of the first original medical data to generate at least some of the first semantically annotated medical data;
   (C) applying a reasoning engine to the first semantically annotated medical data to generate a first instance of a first disease-specific semantic model;
      wherein the first instance of the first disease-specific semantic model includes data representing a medical history of the first patient; and
      wherein the first instance of the first disease-specific semantic model includes data explicitly representing a medical condition of the first patient, wherein the first original medical data does not include data explicitly representing the medical condition of the first patient; and
      wherein applying the reasoning engine to the first semantically annotated medical data to generate the first instance of the first disease-specific semantic model comprises generating the data explicitly representing the medical condition of the first patient based on the first semantically annotated medical data;
   (D) updating an NLP model in the NLP module to produce an updated NLP module;
   (E) generating a new version of the first instance of the first disease-specific semantic model based on the updated NLP module;
   (F) evaluating the new version of the first instance of the first disease-specific semantic model against a plurality of criteria associated with a first clinical trial,
      wherein the first disease-specific semantic model has a plurality of attributes, each of which has a corresponding range of permissible values;
      wherein the new version of the first instance of the first disease-specific semantic model has the plurality of attributes, and wherein each of the plurality of attributes in the new version of the first instance of the first disease-specific semantic model has a corresponding value within the corresponding range of permissible values;
      the evaluating comprising calculating a semantic distance between the new version of the first instance of the first disease-specific semantic model and the plurality of criteria associated with the first clinical trial; and
   (G) determining, based on the evaluation, whether the new version of the first instance of the first disease-specific semantic model satisfies the plurality of criteria associated with the first clinical trial.

2. The method of claim 1:
   wherein (G) comprises generating, based on a rule, data representing a conclusion whether the new version of the first instance of the first disease-specific semantic model satisfies the plurality of criteria associated with the first clinical trial; and
   wherein the method further comprises:
      (H) identifying the rule; and
      (I) storing an association between the rule and the conclusion.

3. The method of claim 1:
   wherein (G) comprises generating, based on a data element, data representing a conclusion whether the new version of the first instance of the first disease-specific semantic model satisfies the plurality of criteria associated with the first clinical trial; and
   wherein the method further comprises:
      (H) identifying the data element; and
      (I) storing an association between the data element and the conclusion.

4. The method of claim 1, further comprising:
   (H) receiving, from a user, input representing feedback on the evaluation; and
   (I) retraining the NLP model in the updated NLP module based on the input received from the user.

5. The method of claim 1, wherein (F) comprises processing the new version of the first instance of the first disease-specific semantic model to generate processed output, and wherein evaluating the new version of the first instance of the first disease-specific semantic model against the plurality of criteria associated with the first clinical trial comprises evaluating the processed output against the plurality of criteria associated with the first clinical trial.

6. The method of claim 5, wherein processing the new version of the first instance of the first disease-specific semantic model comprises generating a summary of the new version of the first instance of the first disease-specific semantic model, and wherein the processed output comprises the summary.

7. The method of claim 5, wherein evaluating the new version of the first instance of the first disease-specific semantic model against the plurality of criteria associated with the first clinical trial comprises evaluating the processed output, and not the new version of the first instance of the first disease-specific semantic model, against the plurality of criteria associated with the first clinical trial.

8. The method of claim 1:
wherein (F) comprises processing the new version of the first instance of the first disease-specific semantic model to generate first processed output, and wherein evaluating the new version of the first instance of the first disease-specific semantic model against the plurality of criteria associated with the first clinical trial comprises evaluating the first processed output against the plurality of criteria associated with the first clinical trial; and
wherein the method further comprises:
(H) processing the new version of the first instance of the first disease-specific semantic model to generate second processed output, wherein the first processed output differs from the second processed output;
(I) evaluating the second processed output against a plurality of criteria associated with a second clinical trial, comprising calculating a semantic distance between the new version of the first instance of the first disease-specific semantic model and the plurality of criteria associated with the second clinical trial, wherein the plurality of criteria associated with the first clinical trial differs from the plurality of criteria associated with the second clinical trial; and
(J) determining, based on the evaluation in (I), whether the new version of the first instance of the first disease-specific semantic model satisfies the plurality of criteria associated with the second clinical trial.

9. A system comprising at least one non-transitory computer-readable medium having computer program instructions stored thereon, the computer program instructions being executable by at least one computer processor to perform a method, the method comprising:
(A) receiving first original medical data associated with a first patient over time;
(B) generating, based on the first original medical data, first semantically annotated medical data associated with the first patient, comprising applying a Natural Language Processing (NLP) engine that uses at least one medical ontology to generate the first semantically annotated medical data based on the first original medical data, wherein applying the NLP engine to the first medical data comprises applying rules to at least some of the first original medical data to generate at least some of the first semantically annotated medical data;
(C) applying a reasoning engine to the first semantically annotated medical data to generate a first instance of a first disease-specific semantic model;
wherein the first instance of the first disease-specific semantic model includes data representing a medical history of the first patient; and
wherein the first instance of the first disease-specific semantic model includes data explicitly representing a medical condition of the first patient, wherein the first original medical data does not include data explicitly representing the medical condition of the first patient; and
wherein applying the reasoning engine to the first semantically annotated medical data to generate the first instance of the first disease-specific semantic model comprises generating the data explicitly representing the medical condition of the first patient based on the first semantically annotated medical data;

(D) updating an NLP model in the NLP module to produce an updated NLP module;
(E) generating a new version of the first instance of the first disease-specific semantic model based on the updated NLP module;
(F) evaluating the new version of the first instance of the first disease-specific semantic model against a plurality of criteria associated with a first clinical trial,
wherein the first disease-specific semantic model has a plurality of attributes, each of which has a corresponding range of permissible values;
wherein the new version of the first instance of the first disease-specific semantic model has the plurality of attributes, and wherein each of the plurality of attributes in the new version of the first instance of the first disease-specific semantic model has a corresponding value within the corresponding range of permissible values;
the evaluating comprising calculating a semantic distance between the new version of the first instance of the first disease-specific semantic model and the plurality of criteria associated with the first clinical trial; and
(G) determining, based on the evaluation, whether the new version of the first instance of the first disease-specific semantic model satisfies the plurality of criteria associated with the first clinical trial.

10. The system of claim 9:
wherein (G) comprises generating, based on a rule, data representing a conclusion whether the new version of the first instance of the first disease-specific semantic model satisfies the plurality of criteria associated with the first clinical trial; and
wherein the method further comprises:
(H) identifying the rule; and
(I) storing an association between the rule and the conclusion.

11. The system of claim 9:
wherein (G) comprises generating, based on a data element, data representing a conclusion whether the new version of the first instance of the first disease-specific semantic model satisfies the plurality of criteria associated with the first clinical trial; and
wherein the method further comprises:
(H) identifying the data element; and
(I) storing an association between the data element and the conclusion.

12. The system of claim 9, wherein the method further comprises:
(H) receiving, from a user, input representing feedback on the evaluation; and
(I) retraining the NLP model in the updated NLP module based on the input received from the user.

13. The system of claim 9, wherein (F) comprises processing the new version of the first instance of the first disease-specific semantic model to generate processed output, and wherein evaluating the new version of the first instance of the first disease-specific semantic model against the plurality of criteria associated with the first clinical trial comprises evaluating the processed output against the plurality of criteria associated with the first clinical trial.

14. The system of claim 13, wherein processing the new version of the first instance of the first disease-specific semantic model comprises generating a summary of the new version of the first instance of the first disease-specific semantic model, and wherein the processed output comprises the summary.

15. The system of claim 13, wherein evaluating the new version of the first instance of the first disease-specific semantic model against the plurality of criteria associated with the first clinical trial comprises evaluating the processed output, and not the new version of the first instance of the first disease-specific semantic model, against the plurality of criteria associated with the first clinical trial.

16. The system of claim 9:
  wherein (F) comprises processing the new version of the first instance of the first disease-specific semantic model to generate first processed output, and wherein evaluating the new version of the first instance of the first disease-specific semantic model against the plurality of criteria associated with the first clinical trial comprises evaluating the first processed output against the plurality of criteria associated with the first clinical trial; and wherein the method further comprises:
  (H) processing the new version of the first instance of the first disease-specific semantic model to generate second processed output, wherein the first processed output differs from the second processed output;
  (I) evaluating the second processed output against a plurality of criteria associated with a second clinical trial, comprising calculating a semantic distance between the new version of the first instance of the first disease-specific semantic model and the plurality of criteria associated with the second clinical trial, wherein the plurality of criteria associated with the first clinical trial differs from the plurality of criteria associated with the second clinical trial; and
  (J) determining, based on the evaluation in (I), whether the new version of the first instance of the first disease-specific semantic model satisfies the plurality of criteria associated with the second clinical trial.

* * * * *